United States Patent [19]

Castelhano et al.

[11] Patent Number: 4,970,297
[45] Date of Patent: Nov. 13, 1990

[54] TRANSGLUTAMINASE INHIBITORS

[75] Inventors: Arlindo L. Castelhano; Diana H. Pliura, both of Mississauga, Canada; Michael C. Venuti, San Francisco, Calif.

[73] Assignee: Syntex (U.S.A.) Inc., Palo Alto, Calif.

[21] Appl. No.: 25,426

[22] Filed: Mar. 13, 1987

[51] Int. Cl.$^5$ .............................................. C07K 5/00
[52] U.S. Cl. .................................................... 530/331
[58] Field of Search ................... 514/378, 380, 18, 19; 530/331, 330; 548/243; 435/212, 219; 424/94; 260/998.2, 998.21

[56] References Cited

U.S. PATENT DOCUMENTS

| | | | |
|---|---|---|---|
| 4,128,542 | 12/1978 | Atherton et al. | 530/331 |
| 4,276,288 | 6/1981 | Etschenberg et al. | 530/331 |
| 4,305,852 | 12/1981 | Garsky | 530/330 |
| 4,397,853 | 8/1983 | Kawakita et al. | 514/378 |
| 4,593,024 | 6/1986 | Lu et al. | 514/380 |
| 4,657,899 | 4/1987 | Rzeszotarski et al. | 514/114 |
| 4,694,016 | 9/1987 | Lu et al. | 514/380 |

OTHER PUBLICATIONS

J. Med. Chem. (1985), 28(5),668–672, Lauridsen et al.
Cancer Chemotherapy Reports, vol. 58, 6 (1974), Cooney et al.
Chem. Abs., vol. 102, 1985, 20 3802 k.
Chem. Abs., vol. 94, 1981, 16038v.
Chem. Abs., vol. 82, 1975, 149188t.
Organic Chemistry, vol. 6, 2nd, pp. 140–141.
Organic Chemistry, 3rd ed., Chap. 36, p. 1152.

*Primary Examiner*—Lester L. Lee
*Assistant Examiner*—T. D. Wessendorf
*Attorney, Agent, or Firm*—Lester E. Johnson; Liza K. Toth; Tom M. Moran

[57] ABSTRACT

This invention is directed to compounds of the formula:

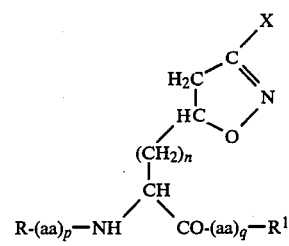

or an optical isomer thereof, or a pharmaceutically acceptable salt thereof, wherein:

n is 0, 1 or 2;

p and q are independently 0, 1 or 2 and the sum of (p+q) is less than or equal to 3;

X is selected from the group consisting of: halo; $-OR^2$, $-SR^2$, $-S(O)R^2$, $-S(O)_2R^2$, and $-S(O)_2NHR^2$, wherein $R^2$ is lower alkyl, mono-, di- or tri-fluoro alkyl of 2 or 3 carbon atoms, optionally substituted aryl;

R is H or an N-protecting group;

$R^1$ is alkylthio, arylthio, amino, alkylamino, optionally substituted arylamino, or optionally substituted aralkylamino; and when the sum of n+p+q is greater than or equal to one, $R^1$ is also hydroxy, alkoxy, or aralkoxy; and each (aa) is independently an α-amino acid residue with an optionally protected amino acid side chain.

22 Claims, No Drawings

TRANSGLUTAMINASE INHIBITORS

BACKGROUND OF THE INVENTION

Transglutaminases are a family of enzymes that catalyze the calcium-dependent, post-translational modification of the γ-carboxamide group of peptide-bound glutamine residues. A key intermediate in the catalysis is a thioester acyl-enzyme complex. An ε-amino group of peptide-bound lysine is the acyl acceptor in protein crosslinking reactions:

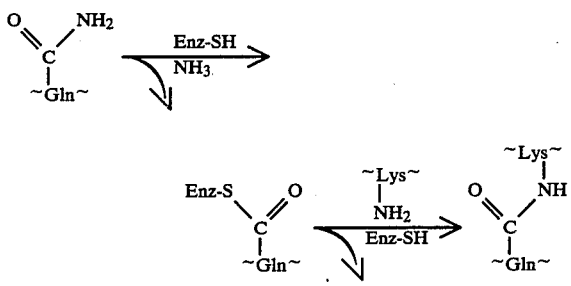

Alternatively, a free amine, such as putrescine, may act as an acyl acceptor resulting in the post-translational modification of proteins.

Transglutaminases have been implicated in a variety of disease states, including acne, psoriasis, cataracts, immunologic disease states, Alzheimer's disease and hyaline membrane disease.

For example, regarding the acne state, changes in transglutaminase activity during comedogenesis have been demonstrated by DeYoung et al., in *J. Investigative Dermatology*, 82, 275 (1984). These investigators have demonstrated that in early acne lesions there is intense transglutaminase activity in the involved sebaceous follicles. In normal follicles no such activity is observed. Furthermore, Dalziel et al., in *Br. J. Exp. Pathology* 65, 107–115 (1984) have shown that the cornified cell envelope, a product of transglutaminase activity, produces chronic inflammation when intradermally injected. The cornified envelope is responsible for the rigid, resistant structure of differentiated squamous cells. The cornified envelopes in acne comedones play an important role in the resistant cohesive nature of these structures and in their inflammatory potential upon rupture. Therefore, a need exists for an inhibitor of transglutaminase effective in the suppression of cornified envelope formation.

With regard to psoriasis, Bernard et al. in British Journal of Dermatology, 114, 279 (1986) have demonstrated, by histochemical activity staining, the precocious distribution of transglutaminase activity down to the suprabasal layer of involved psoriatic epidermis. In addition, the distribution of involucrin, one of the major substrates for epidermal transglutaminase, matches the distribution of transglutaminase activity. Thus, in psoriasis, there is an apparent loss of integrated control of the independent pathways for terminal differentiation of keratinocytes, and the onset of involucrin and transglutaminase activity is favored. A need exists for effective transglutaminase inhibitors to modulate the elevated transglutaminase activity in psoriatic epidermis.

Hereditary cataractous rat lenses show significantly elevated transglutaminase activities (2.7 to 17.7 times higher specific activities for young and old animals respectively). See Azari, P. et al., *Current Eye Res*, 1, 463 (1981).

With respect to immunologic disease states, much research has been directed to the role of transglutaminases in receptor functions, mitogen-induced cell activation and immune recognition. See Fesus, L. *Surv. Immunol. Res.* 1, 297–304 (1982).

Regarding Alzheimer's disease, neuronal transglutaminase is a likely mediator of the apparently irreversible crosslinking of neuronal proteins leading to the formation of paired helical fragments, which are a distinctive pathological feature of Alzheimer's disease. See Selkoe, et al., *Science*, 215, 1243–1245 (1982), Selkoe, et al., *Proc. Natl. Acad. Sci., U.S.A.*, 79, 6070–6074 (1982), and Schlaepfer, "Biological Aspects of Alzheimer's Disease," (Ed. Katzman) p. 155, Cold Spring Harbour Laboratory. Bundles of paired helical fragments form neural fibrillary tangles, and the number of neuritic plaques correlates to the degree of intellectual impairment. See Farmer, et al. in *J. Neuropathol. Exp. Neurol.* 35, 367 (1976).

Previously reported inhibitors of transglutaminase include alternate substrate inhibitors, covalent inactivators and active site directed inhibitors. The alternate substrate inhibitors include alkyl primary amines, such as monodansylcadaverine, and alternative acyl-donors, such as beta-phenyl propionylthiocholine. These inhibitors prevent protein crosslinking, but do not prevent post-translational modification of proteins. They suffer from the drawback that they are effective only in relatively high concentrations, i.e., at $10^{-3}$M or higher. The covalent inhibitors include alkyl isocyanates, such as $(CH_3)_2-CH-CH_2-N=C=O$, as titrants of active site cysteine residues, but these lack specificity for transglutaminases. An active site directed inhibitor is cystamine, which lacks specificity for transglutaminases and is effective only at concentrations of greater than $10^{-3}$M.

Accordingly, a need exists for specific and potent inactivators of transglutaminases.

SUMMARY OF THE INVENTION

This invention is directed to compounds of the formula:

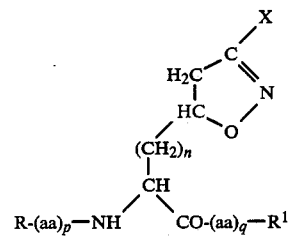

or an optical isomer thereof, or a pharmaceutically acceptable salt thereof, wherein:

n is 0, 1 or 2;

p and q are independently 0, 1 or 2 and the sum of (p+q) is less than or equal to 3;

X is selected from the group consisting of: halo; $-OR^2$, $-SR^2$, $-S(O)R^2$, $-S(O)_2R^2$, and $-S(O)_2NHR^2$, wherein $R^2$ is lower alkyl, mono-, di- or tri-fluoro alkyl of 2 or 3 carbon atoms, optionally substituted aryl;

R is H or an N-protecting group;

$R^1$ is alkylthio, arylthio, amino, alkylamino, optionally substituted arylamino, or optionally substituted aralkylamino; and when the sum of $n+p+q$ is greater than or equal to one, $R^1$ is also hydroxy, alkoxy, or aralkoxy; and each (aa) is independently an α-amino acid residue with an optionally protected amino acid side chain.

Another aspect of the invention is directed to a method for treating acne in humans, said method comprising the step of administering a therapeutically effective amount of a compound of Formula I to a human.

Another aspect of the invention is directed to a method for treating cataracts in humans, said method comprising the step of administering a therapeutically effective amount of a compound of Formula I to a human.

Another aspect of the invention is directed to a method for treating Alzheimer's disease in humans, said method comprising the step of administering a therapeutically effective amount of a compound of Formula I to a human.

Another aspect of the invention is directed to a method for treating immunosuppressive diseases characterized by elevated transglutaminase activity in humans, said method comprising the step of administering a therapeutically effective amount of a compound of Formula I to a human.

Another aspect of the invention is directed to a method for treating helminthic infections in mammals, said method comprising the step of administering a therapeutically effective amount of a compound of Formula I to a mammal.

DETAILED DESCRIPTION

Definitions

For the purposes of this invention, the following terms are to be understood to have the meanings set forth below.

"Alkyl" means a branched or unbranched, saturated aliphatic hydrocarbon radical, having the number of carbon atoms specified, or if no number is specified, having up to 8 carbon atoms. The prefix "alk-" is also indicative of a radical having up to 8 carbon atoms in the alkyl portion of that radical, unless otherwise specified. Examples of alkyl radicals include methyl, ethyl, n-propyl, isopropyl, n-butyl, tert-butyl, n-pentyl, n-hexyl, and the like. The terms "lower alkyl" and "alkyl of 1 to 4 carbon atoms" are synonymous and used interchangeably.

Abbreviations are used herein as follows:
"Ac" means acetyl.
"Ala" means alanyl.
"Boc" means t-butyloxycarbonyl.
"BOC-ON" is [2-(tertbutoxycarbonyloxyimino)-2-phenylacetylnitrile].
"CBZ" means benzyloxycarbonyl.
"DCC" means N,N'-dicyclohexylcarbodiimide.
"DMAP" means 4-dimethylaminopyridine.
"EDCI" means 1-(3-dimethylaminopropyl)-3-ethylcarbodiimide.
"FMOC" means 9-fluorenylmethyloxycarbonyl.
"Gly" means glycyl.
"MNP" means (6-methoxy-2-naphthyl)-2'-propionyl.
"Nic" means nicotinyl.
"NMM" means N-methylmorpholine.
"Phe" means phenylalanyl.
"Ser" means seryl.

"Tosyl" means 4-toluenesulfonyl.
"Aryl" means phenyl, 1-naphthyl or 2-naphthyl.
"Aralkyl" means an aryl radical as defined above, attached to a lower alkyl radical. Examples are benzyl, naphthylmethyl, 2-naphthyl-1'-ethyl (i.e., 2-position on the naphthyl and 1' position on the ethyl radical), 2-naphthyl-2'-ethyl, and the like. The lower alkyl radical bridging the aryl radical to the rest of the molecule can be straight or branched.

"Arylamino" and "Aralkylamino" are commensurate in scope with aryl and aralkyl as defined above, but the aryl or aralkyl radical attached to an amino moiety at the designated position.

"Arylthio" and "alkylthio" are similarly commensurate in scope with aryl and alkyl as defined above, but the aryl or alkyl radical is attached to a sulfur radical.

"α-Amino acids" as used herein include the principal naturally occurring and commercially available amino acids and optical isomers thereof. Typical examples of such amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, 5-hydroxytryptophan, 4-chlorophenylalanine, 4-fluorophenylalanine, 4-iodophenylalanine, 3,4-dihydroxyphenylalanine, 3-methoxy-4-hydroxyphenylalanine, homophenylalanine, phenylglycine, o-, m-, and p-tyrosine, tryptophan, glutamine, asparagine, proline and hydroxyproline.

An amino acid residue is an amino acid radical —NHCH($R^3$)C(O)—, wherein $R^3$ is an amino acid side chain, except for the amino acid residues of proline and hydroxyproline which are —N(CH$_2$CH$_2$CH$_2$)CHC(O)— and —N(CH$_2$CHOHCH$_2$)CHC(O)—, respectively. Thus, an amino acid residue is:

(1) a radical of formula II

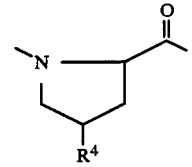

(II)

wherein $R^4$ is hydrogen or hydroxy; or (2) a radical of formula III

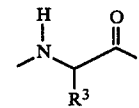

(III)

wherein $R^3$ is hydrogen or hydroxy and $R^3$ is an optionally protected amino acid side chain defined below.

An amino acid side chain is a radical found on the α-carbon of an α-amino acid as defined herein, corresponding to $R^3$ herein An "α-amino acid residue with an optionally protected amino acid side chain" means an α-amino acid residue, as defined above, having an optionally protected α-amino side chain, $R^3$, wherein $R^3$ is selected from the group consisting of:
(a) hydrogen;
(b) lower alkyl;

(c) —$(CHR^5)_m WR^6$ wherein m is 1 or 2, W is oxygen or sulfur and $R^5$ and $R^6$ are independently hydrogen or methyl;

(d) —$CH(CH_3)OCH_2C_6H_5$;

(e) —$(CH_2)_k C(O)Y$ wherein k is 1 or 2 and Y is hydroxy, amino, alkoxy or aralkoxy;

(f) —$(CH_2)_r NHCH(NHR^7)NR^8$ wherein r is 2, 3 or 4 and $R^7$ and $R^8$ are independently hydrogen or lower alkyl;

(g) —$(CH_2)_s NH_2$ wherein s is 2, 3, 4 or 5;

(h) —$(CH_2)_4 NHCOOC(CH_3)_3$;

(i) —$(CH_2)_2 CHOHCH_2 NH_2$;

(j) a radical of formula IV —$(CH_2)_t$—P  (IV)
wherein t is 1 or 2 and P is optionally substituted phenyl; and (k) a radical chosen from

[chemical structures]

wherein $R^9$ is hydrogen or an N-protecting group for imidazole or indole functionality; $R^{10}$ is hydrogen, hydroxy or methoxy; and Z is hydrogen, hydroxy or O-protected hydroxy.

"Alkoxy" means an alkyl radical of up to 8 carbon atoms unless otherwise specified, that is attached to an oxygen radical, which is in turn attached to the structure provided. Examples are methoxy, ethoxy, propoxy, n-butoxy, isobutoxy, tert-butoxy, n-pentoxy, n-hexoxy, n-heptoxy, n-octoxy, and the like.

"Alkoxycarbonyl" means an alkoxy radical (as defined above) attached to a carbonyl radical, which in turn is attached to the structure provided. Examples are methoxycarbonyl, ethoxycarbonyl, propoxycarbonyl, n-butoxycarbonyl, isobutoxycarbonyl, tert-butoxycarbonyl, n-pentoxycarbonyl, n-hexoxycarbonyl, n-heptoxycarbonyl, n-octoxycarbonyl, and the like.

"Aralkoxy" means an aralkyl radical (as defined above) that is attached to an oxygen radical, which is in turn attached to the structure provided. Examples are benzyloxy, naphthylmethoxy, and the like.

"Halo" means bromo, chloro or fluoro.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Optionally substituted aryl" means optionally substituted phenyl, 1-naphthyl or 2-naphthyl. "Optionally substituted arylamino" and "optionally substituted aralkylamino" are of the same scope, in that the optional substituents are on the aryl ring and are as defined in the next two paragraphs.

"Optionally substituted phenyl" means unsubstituted phenyl; and phenyl having 1 to 3 substituents, where the substituents are independently selected from the group consisting of lower alkyl, lower alkoxy, nitro, halo, acetyl, benzoyl, hydroxy, amino, methylamino, dimethylamino, diethylamino, methylthio, cyano, trifluoromethyl, —COOH, —$CONH_2$, —$C(NH)NH_2$, —$C(NR^{11})NH_2$, —$C(NH)NHR^{11}$, —$C(NR^{11})NHR^{11}$, —$COOR^{11}$, and —$NHCOR^{11}$ wherein $R^{11}$ is lower alkyl.

"Optionally substituted 1-naphthyl or 2-naphthyl" includes unsubstituted 1-naphthyl, unsubstituted 2-naphthyl, and 1-naphthyl or 2-naphthyl substituted at the 6-position with hydroxy or lower alkoxy.

An "O-, or N-protecting group" is a radical attached to an oxygen or nitrogen atom, respectively, which radical serves to protect the oxygen or nitrogen functionality against undesired reactions and/or to modify the properties of the molecule to which it is attached (e.g., solubility, lipophilicity, bioavailability, etc.). Such protecting groups are well known in the art and are described in *The Peptides*, E. Gross and J. Meienhofer, Eds., 3, Academic Press, N.Y. (1981), and *Chemistry of the Amino Acids*, J. P. Greenstein and M. Winitz, Ed., 2, J. Wiley and Sons, N.Y. (1961).

"N-Protecting groups" for amine functionalities of amino acids, at the peptide N-terminal, or on amino acid side chains are well known in the art. An exemplification of known amino N-protecting groups is included in *The Peptides*, E. Gross and J. Meienhofer, Eds., 3, Chapter 1, Academic Press, N.Y. (1981); *Protective Groups in Organic Synthesis*, T. W. Greene, J. Wiley and Sons, N.Y., Chapter 7, (1981); and *Chemistry of the Amino Acids*, J. P. Greenstein and M. Winitz, J. Wiley and Sons, N.Y., 2, pp. 885–924 (1961). Typical of such protecting groups include Boc, CBZ, Fmoc, phthaloyl, benzoyl, mesyl, tosyl, and the like.

More specifically, the substituent R at the amino terminus of $(aa)_p$ or at the NH group as shown in Formula I can be selected from:

(1) hydrogen;
(2) alkyl;
(3) lower alkyl sulfonyl;
(4) aryl sulfonyl;
(5) aryl sulfonyl substituted with lower alkyl on the aryl moiety;
(6) 9-fluorenylmethyloxycarbonyl;
(7) a radical of the formula:

$$R^{12}-\overset{O}{\underset{\|}{C}}- \quad \text{(II)}$$

wherein:

$R^{12}$ is hydrogen; alkyl of 1 to 4 carbon atoms; pyridinyl; furanyl; adamantyloxy; alkoxy; aryl; aryl substituted with up to 2 substituents where the substituents are independently halo, lower alkyl, alkoxy, nitro, trifluoromethyl, carboxyl, or alkoxycarbonyl; aralkyl; aralkyl substituted on the aryl radical with up to 2 substituents independently selected from hydroxy, alkoxy and halo; aralkoxy; aralkoxy substituted on the aryl radical with up to 2 substituents independently selected from halo, lower alkyl, alkoxy, nitro, and trifluoromethyl; or optionally substituted aralkylamino.

"N-protecting groups" for imidazole functionalities on histidine amino acid side chains are known in the art and described in *The Peptides*, 3, pp. 70–80, and *Chemistry of the Amino Acids*, 2, pp. 1060–1068, as cited earlier. These include the benzyl, triphenylmethyl (trityl), 2,4-dinitrophenyl, p-toluenesulfonyl, benzoyl, and CBZ N-protecting groups.

"N-protecting groups" for indole functionalities on tryptophan amino acid side chains are known in the art and described in *The Peptides*, 3, pp. 82–84, as cited earlier. These include the formyl and CBZ N-protecting groups.

"O-protecting groups" for hydroxy functionalities on amino acid side chains are known in the art and described in *The Peptides*, 3, pp. 169–201, and *Chemistry of the Amino Acids*, 2, pp. 1050–1056, as cited earlier. For aromatic hydroxy functionalities, suitable O-protecting groups include the benzyl, tert-butyl, methyl, CBZ, and tosyl groups.

"S-protecting groups" for thiol functionalities on amino acid side chains are known in the art and described in *The Peptides*, 3, pp. 137–167, and *Chemistry of the Amino Acids*, pp. 1077–1092, as cited earlier. These include methyl and benzyl groups.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

The compounds of the present invention may be single stereoisomers, racemates, or mixtures of diastereomers. In instances where the stereochemistry is not specified, it should be understood to include all of the single stereoisomers taken separately, or the racemates, or mixtures of diastereomers.

The compounds of this invention are named as dihydroisoxazole derivatives of an optionally protected glycine (when n=0), alanine (when n=1), or "homoalanine" (when n=2) amino acid residue or a peptide including same. The protecting group R (see Formula I), if any, is recited first. In cases where there is no intervening amino acid corresponding to (aa)$_p$, the 3-substituted, 4,5-dihydroisoxazole moiety is then named as a substituent off the α-carbon of glycine, the β-carbon atom of alanine, or the γ-carbon of homoalanine. In cases where there is no intervening amino acid corresponding to (aa)$_q$, the substituent R$^1$ is named. The name of the R$^1$ substituent will be in the form of an amide when R$^1$ is joined to the molecule by an amino functionality because of the presence of the terminal carbonyl group of the derivatized amino acid. This nomenclature system is used as a matter of convenience, and exemplified below.

The name, "N-benzyloxycarbonyl-β-D,L-(3-bromo-4,5-dihydroisoxazol-5-yl)alanine(4-(ethoxycarbonyl)-phenyl)amide" (Example 4) represents the structure:

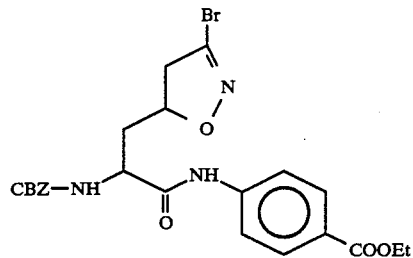

A similar structure, except with CBZ replaced by BOC, is named and made in Example 1.

The name, "N-benzyloxycarbonyl-β-(3-bromo-4,5-dihydroisoxazol-5-yl)alanine" (Example 2) represents a similar structure excluding the 4-(ethoxycarbonyl)-phenylamino substituent on the carbonyl functionality (the right hand end of the molecule as drawn terminates with a simple —OH).

Where an amino acid residue —(aa)$_p$— or —(aa)$_q$— precedes or follows the derivatized alanyl residue, it is so indicated. For example, the name, "N-benzyloxycarbonyl-D,L-β-(3-bromo-4,5-dihydroisoxazol-5-yl)alanyl glycine ethyl ester (Example 5) represents the structure:

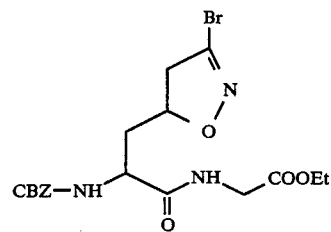

As can readily be ascertained, this structure corresponds to Formula I where R is CBZ, p is zero, n is 1, (aa)$_q$ is glycinyl, and R$^1$ is ethoxy.

A similar structure, except with a hydrogen atom replacing the ethyl radical on the left hand side of the molecule as drawn, is named and made in Example 8.

The name, "N-tert-butoxycarbonyl-L-alanyl-β-(3-bromo-4,5-dihydroisoxazol-5-yl)alanine," (Example 7), signifies the compound of Formula I wherein R is the Boc protecting group, (aa)$_p$ is the alanyl amino acid residue, n is 1, q is zero, and $R^1$ is hydroxy.

PREFERRED EMBODIMENTS

Within the broadest scope of this invention, several embodiments are particularly preferred. While this section sets forth general guidelines as to such embodiments, equivalent embodiments will be apparent to one of ordinary skill in the art and should not be construed as excluded from the preferred classes of compounds exemplified below.

Accordingly, in the preferred embodiments X is halo, such as bromo or chloro, although the other leaving groups set forth in the Summary of the Invention could be substituted.

R is preferably an N-protecting group of the formula

wherein $R^{12}$ is aralkyl or aralkoxy, where the aryl ring of the aralkyl or aralkoxy radical is either unsubstituted, or substituted with substituents as set forth in part (7) of the definition of R, above. Examples of R are para-methoxy-CBZ, ortho-chloro-CBZ, unsubstituted CBZ, 1-naphthylacetyl, 2-naphthylacetyl, or 2-naphthyl-2'-propionyl (2-position on the naphthyl and 2' position on the propionyl radical), where in each case including a naphthyl radical, the naphthyl radical is optionally substituted with methoxy at the 6-position of the naphthyl radical. Other preferred N-protecting groups are Boc and nicotinyl.

The number of methylene groups, n, between the dihydroisoxazole ring and the α-carbon of the derivatized alanine residue, is preferably 0 or 1, although 2 is acceptable.

It is generally preferred that p and q each be 0 or 1, yielding at most a tripeptide, although a tetra-peptide would be acceptable. Generally, each (aa) is preferably an α-amino acid residue with an unprotected side chain. When p is 1 it is generally more preferred that (aa)$_p$ be an aromatic amino acid residue, such as phenylalanyl, tyrosyl, or tryptophanyl; additionally, 5-hydroxytryptophanyl, and 4-hydroxy-3-methoxy phenylalanyl are among the more preferred residues; and most particularly preferred for (aa)$_p$ is L-phenylalaninyl; and when q is 1 it is more preferred that (aa)$_q$ be seryl or glycyl, most preferably seryl.

$R^1$ is preferably an optionally substituted arylamino or aralkylamino functionality (i.e., yielding a corresponding amide at the carboxy terminus of the molecule), or a hydroxy, alkoxy or aralkoxy functionality provided that the sum of n+p+q is not zero.

In light of the foregoing, preferred embodiments of the invention are directed to compounds of the formula:

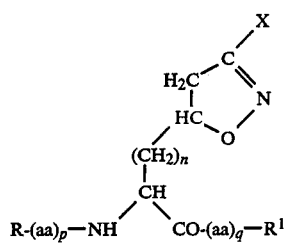

or an optical isomer thereof, or a pharmaceutically acceptable salt thereof, wherein:
n is 0 or 1;
p and q are independently 0 or 1;
X is chloro or bromo;
R is an N-protecting group of the formula $$R^{12}-\overset{O}{\underset{\|}{C}}- \quad (II)$$

wherein $R^{12}$ is aralkyl optionally substituted on the aryl ring with up to 2 substituents independently selected from hydroxy, alkoxy and halo; or aralkoxy optionally substituted on the aryl ring with up to 2 substituents independently selected from halo, lower alkyl, alkoxy, nitro and trifluoromethyl;

$R^1$ is alkylamino, optionally substituted arylamino, or optionally substituted aralkylamino; and when the sum of n+p+q is at least one, $R^1$ is also hydroxy, alkoxy, or aralkoxy; and each (aa) is independently an α-amino acid residue selected from the group consisting of glycyl, alanyl, seryl, homoseryl, threonyl, valyl, norvalyl, leucyl, isoleucyl, norleucyl, aspartic acid, glutamic acid, lysyl, ornithyl, histidyl, arginyl, cysteinyl, homocysteinyl, methionyl, phenylalanyl, 5-hydroxytryptophanyl, 4-chlorophenylalanyl, 4-fluorophenylalanyl, 4-iodo-phenylalanyl, 3,4-dihydroxyphenylalanyl, 3-methoxy-4-hydroxyphenylalanyl, homophenylalanyl, phenylglycyl, o-tyrosyl, m-tyrosyl, p-tyrosyl, tryptophanyl, glutamyl, asparagyl, prolyl and hydroxyprolyl.

In the most preferred embodiments, n is generally 0 or 1; R is generally CBZ or aralkylcarbonyl optionally substituted on the aryl ring, such as 6-methoxy-2-naphthyl-2'-propionyl; (aa)$_p$ is L-phenylalanyl or p is zero; (aa)$_q$ is seryl or glycyl or q is zero; and $R^1$ is alkoxy, hydroxy, optionally substituted arylamino such as ortho- or para-ethoxycarbonylphenylamino, or optionally substituted aralkylamino, such as benzylamino, 3,4-dimethoxybenzylamino or 3-aminobenzylamino.

Specific examples of preferred embodiments have the following substitution patterns for $R^I$, $R^{II}$, n and X where $R^I$=R—(aa)$_p$— and $R^{II}$=$R^1$—(aa)$_q$— in Formula I.

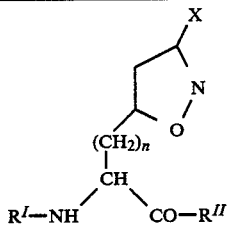

(I)

| $R^I$ | $R^{II}$ | n | X | DIASTEREOMERS | MP | alpha |
|---|---|---|---|---|---|---|
| CBZ-(L)Phe | OMe | 0 | Br | mixture (2) | | |
| CBZ | Ser-OEt | 1 | Br | 2 most polar | 106–121 | |
| CBZ | NH—C₆H₄-(p)COOEt | 1 | Br | mixture (4) | 116–117 | |
| CBZ-(L)Phe | Gly-OEt | 1 | Br | mixture | 155–162 | |
| CBZ | NH—CH₂—C₆H₅ | 1 | Br | mixture (4) | 105–107 | |
| CBZ | Ser-OEt | 1 | Br | 2 least polar | 114–119 | |
| CBZ | OMe | 1 | Br | mixture | oil | |
| CBZ | NH—C₆H₄-(m)COOEt | 1 | Br | mixture (4) | | |
| CBZ | NH—C₆H₄-(o)COOEt | 1 | Br | mixture (4) | | |
| CBZ-(L)Phe | NH—CH₂C₆H₅ | 1 | Br | mixture | 162–168 | |
| CBZ-(L)Phe | OMe | 0 | Br | less polar | | |
| CBZ | OH | 1 | Br | alpha-R (2) | | |
| CBZ | Ser-OEt | 1 | Br | mixture | 70–82 | |
| Nic | OMe | 1 | Br | more polar | | |
| CBZ | OH | 1 | Br | more polar (D) | | +65.54 |
| CBZ-(L)Phe | OMe | 0 | Br | more polar | | |
| CBZ | OH | 1 | Br | less polar(D) | | −34.5 |
| CBZ-(L)Phe | OH | 1 | Br | mixture | | |
| CBZ | OH | 1 | Br | more polar (2) | 158–158.5 | |
| H.TsOH | NH—C₆H₄-(p)COOEt | 1 | Br | mixture | | |
| CBZ | OMe | 2 | Br | mixture | oil | |
| CBZ | OH | 1 | Br | less polar(L) | | +39 |
| CBZ | OH | 1 | Br | mixture (4) | 140–145d | |
| CBZ | NHCH₂C₆H₃(3,4-di-OMe) | 1 | Br | mixture | | |
| CBZ | OH | 1 | Br | less polar (2) | 153–154 | |
| CBZ | OH | 1 | Br | Alpha-S (2) | 137–138 | |
| CBZ-(L)Phe | NH—C₆H₄-(p)COOEt | 1 | Br | mixture | | |
| CBZ | NH—CH₂—C₆H₄-(m)NH₂ | 1 | Br | less polar | 50–55 | |
| CBZ | Gly-OEt | 1 | Br | mixture (4) | | |
| CBZ | O—CH₂—C₆H₅ | 1 | Br | mixture (4) | 63 | |
| CBZ | NH—CH₂—C₆H₄-(m)NH₂ | 1 | Br | more polar | 85–88 | |
| CBZ | OH | 1 | Br | more polar(L) | | −62.55 |
| CBZ | Gly-OH | 1 | Br | mixture (4) | | |
| CBZ | Gly-Gly-OEt | 1 | Br | mixture | 38–46 | |
| CBZ | NH—C₆H₄-(p)COOEt | 1 | Cl | less polar | | |
| CBZ | NH—C₆H₄-(p)COOEt | 1 | Cl | more polar | | |
| Nic | OMe | 1 | Br | less polar | | |
| Boc | NH—C₆H₄-(p)COOEt | 1 | Br | mixture | | |
| H | NH—C₆H₄-(p)COOEt | 1 | Cl | mixture | 125–130 | |
| CBZ-(L)Phe | NH—C₆H₄-(p)COOEt | 1 | Cl | mixture | 180–182 | |
| CBZ-Gly | NH—C₆H₄-(p)COOEt | 1 | Cl | mixture | 149–152 | |
| Boc-Ala | OH | 1 | Br | mixture | | |
| Ala | OH | 1 | Br | mixture | | |
| CBZ-(L)Phe | Gly-OH | 1 | Br | mixture | 151–154 | |
| MNP | NH—C₆H₄-(p)COOEt | 1 | Br | less polar | | |
| MNP | NH—C₆H₄-(p)COOEt | 1 | Br | more polar | | |

N-Benzyloxycarbonyl-(L)-phenylalanyl-D,L-α-(3-bromo-4,5-dihydroisoxazol-5-yl)-glycine methyl ester;

N-Benzyloxycarbonyl-D,L-β-(3-bromo-4,5-dihydroisoxazol-5-yl)-alanyl serine ethyl ester;

N-Benzyloxycarbonyl-D,L-β-(3-bromo-4,5-dihydroisoxazol-5-yl)-alanine (4-(ethoxycarbonyl)phenyl)amide;

N-Benzyloxycarbonyl-(L)-phenylalanyl-D,L-β-(3-bromo-4,5-dihydroisoxazol-5-yl)-alanyl glycine ethyl ester;

N-Benzyloxycarbonyl-D,L-β-(3-bromo-4,5-dihydroisoxazol-5-yl)-alanine benzylamide;

N-Benzyloxycarbonyl-D,L-β-(3-bromo-4,5-dihydroisoxazol-5-yl)-alanine methyl ester;

N-Benzyloxycarbonyl-D,L-β-(3-bromo-4,5-dihydroisoxazol-5-yl)-alanine (3-(ethoxycarbonyl)phenyl)amide;

N-Benzyloxycarbonyl-D,L-β-(3-bromo-4,5-dihydroisoxazol-5-yl)-alanine (2-(ethoxycarbonyl)phenyl)amide;

N-Benzyloxycarbonyl-(L)-phenylalanyl-D,L-β-(3-bromo-4,5-dihydroisoxazol-5-yl)-alanine benzylamide;

N-Benzyloxycarbonyl-D-β-(3-bromo-4,5-dihydroisoxazol-5-yl)-alanine;

N-Benzyloxycarbonyl-L-β-(3-bromo-4,5-dihydroisoxazol-5-yl)-alanine;

N-Benzyloxycarbonyl-D,L-β-(3-bromo-4,5-dihydroisoxazol-5-yl)-alanine;

N-Nicotinyl-D,L-β-(3-bromo-4,5-dihydroisoxazol-5-yl)-alanine methyl ester;

N-Benzyloxycarbonyl-(L)-phenylalanyl-D,L-β-(3-bromo-4,5-dihydroisoxazol-5-yl)-alanine;

D,L-β-(3-bromo-4,5-dihydroisoxazol-5-yl)-alanine (4-(ethoxycarbonyl)phenyl) amide, toluene sulfonic acid;

N-Benzyloxycarbonyl-D,L-gamma-(3-bromo-4,5-dihydroisoxazol-5-yl)-homoalanine methyl ester;

N-Benzyloxycarbonyl-(L)-phenylalanyl-D,L-β-(3-bromo-4,5-dihydroisoxazol-5-yl)-alanine (4-(ethoxycarbonyl)phenyl)amide;

N-Benzyloxycarbonyl-D,L-β-(3-bromo-4,5-dihydroisoxazol-5-yl)-alanine (3-aminobenzyl) amide;

N-Benzyloxycarbonyl-D,L-β-(3-bromo-4,5-dihydroisoxazol-5-yl)-alanyl glycine ethyl ester;

N-Benzyloxycarbonyl-D,L-β-(3-bromo-4,5-dihydroisoxazol-5-yl)-alanine benzyl ester;

N-Benzyloxycarbonyl-D,L-β-(3-bromo-4,5-dihydroisoxazol-5-yl)-alanyl glycine;

N-Benzyloxycarbonyl-D,L-β-(3-bromo-4,5-dihydroisoxazol-5-yl)-alanyl glycyl glycyl ethyl ester;

N-Benzyloxycarbonyl-D,L-β-(3-chloro-4,5-dihydroisoxazol-5-yl)-alanine (4-(ethoxycarbonyl)phenyl) amide;

N-Tert-butyloxycarbonyl-D,L-β-(3-bromo-4,5-dihydroisoxazol-5-yl)-alanine (4-(ethoxycarbonyl)phenyl) amide;

D,L-β-(3-chloro-4,5-dihydroisoxazol-5-yl)-alanine (4-(ethoxycarbonyl)phenyl) amide;

N-Benzyloxycarbonyl-(L)-phenylalanyl-D,L-β-(3-chloro-4,5-dihydroisoxazol-5-yl)-alanine (4-(ethoxycarbonyl)phenyl) amide;

N-Benzyloxycarbonyl-glycyl-D,L-β-(3-chloro-4,5-dihydroisoxazol-5-yl)-alanine (4-ethoxycarbonyl)phenyl) amide;

N-tert-Butyloxycarbonyl-(L)-alanyl-D,L-β-(3-bromo-4,5-dihydroisoxazol-5-yl)alanine;

(L)-Alanyl-D,L-β-(3-bromo-4,5-dihydroisaxzol-5-yl)alanine;

N-Benzyloxycarbonyl-(L)-phenylalanyl-D,L-β-(3-bromo-4,5-dihydroisoxazol-5-yl)-alanyl-glycine;

N-((6-Methoxy-2-naphthyl)-2-propionyl)-D,L-β-(3-bromo-4,5-dihydroisoxazol-5-yl)-alanine 4-(ethoxycarbonyl)phenyl) amide; and N-Benzyloxycarbonyl-D,L-β-(3-bromo-4,5-dihydroisoxazol-5-yl)alanine (3,4-dimethoxybenzyl) amide.

Amongst the foregoing, currently more preferred are:

N-Benzyloxycarbonyl-(L)-phenylalanyl-D,L-α-(3-bromo-4,5-dihydroisoxazol-5-yl)-glycine methyl ester;

N-Benzyloxycarbonyl-D,L-β-(3-bromo-4,5-dihydroisoxazol-5-yl)-alanyl serine ethyl ester;

N-Benzyloxycarbonyl-D,L-β-(3-bromo-4,5-dihydroisoxazol-5-yl)-alanine (4-(ethoxycarbonyl)phenyl)amide;

N-Benzyloxycarbonyl-(L)-phenylalanyl-D,L-β-(3-bromo-4,5-dihydroisoxazol-5-yl)-alanyl glycine ethyl ester;

N-Benzyloxycarbonyl-D,L-β-(3-bromo-4,5-dihydroisoxazol-5-yl)-alanine benzylamide;

N-Benzyloxycarbonyl-D,L-β-(3-bromo-4,5-dihydroisoxazol-5-yl)-alanine methyl ester;

N-Benzyloxycarbonyl-D,L-β-(3-bromo-4,5-dihydroisoxazol-5-yl)-alanine (3-(ethoxycarbonyl)phenyl) amide;

N-Benzyloxycarbonyl-D,L-β-(3-bromo-4,5-dihydroisoxazol-5-yl)-alanine (2-(ethoxycarbonyl)phenyl) amide;

N-Benzyloxycarbonyl-(L)-phenylalanyl-D,L-β-(3-bromo-4,5-dihydroisoxazol-5-yl)-alanine benzylamide;

D,L-β-(3-bromo-4,5-dihydroisoxazol-5-yl)-alanine (4-(ethoxycarbonyl)phenyl) amide, toluene sulfonic acid;

N-Benzyloxycarbonyl-D,L-β-(3-bromo-4,5-dihydroisoxazol-5-yl)-alanine (3-aminobenzyl) amide;

N-Benzyloxycarbonyl-D,L-β-(3-bromo-4,5-dihydroisoxazol-5-yl)-alanyl glycine ethyl ester;

N-tert-Butyloxycarbonyl-(L)-alanyl-D,L-β-(3-bromo-4,5-dihydroisoxazol-5-yl)alanine;

(L)-Alanyl-D,L-β-(3-bromo-4,5-dihydroisaxzol-5-yl)alanine;

N-Benzyloxycarbonyl-(L)-phenylalanyl-D,L-β-(3-bromo-4,5-dihydroisoxazol-5-yl)-alanyl-glycine;

N-((6-Methoxy-2-naphthyl)-2-propionyl)-D,L-β-(3-bromo-4,5-dihydroisoxazol-5-yl)-alanine 4-(ethoxycarbonyl)phenyl) amide; and N-Benzyloxycarbonyl-D,L-β-(3-bromo-4,5-dihydroisoxazol-5-yl)alanine (3,4-dimethoxybenzyl) amide.

Additionally, the chloro analogs of the foregoing are preferred, i.e.:

N-Benzyloxycarbonyl-(L)-phenylalanyl-D,L-α-(3-chloro-4,5-dihydroisoxazol-5-yl)-glycine methyl ester;

N-Benzyloxycarbonyl-D,L-β-(3-chloro-4,5-dihydroisoxazol-5-yl)-alanyl serine ethyl ester;

N-Benzyloxycarbonyl-D,L-β-(3-chloro-4,5-dihydroisoxazol-5-yl)-alanine (4-(ethoxycarbonyl)phenyl)amide;

N-Benzyloxycarbonyl-(L)-phenylalanyl-D,L-β-(3-chloro-4,5-dihydroisoxazol-5-yl)-alanyl glycine ethyl ester;

N-Benzyloxycarbonyl-D,L-β-(3-chloro-4,5-dihydroisoxazol-5-yl)-alanine benzylamide;

N-Benzyloxycarbonyl-D,L-β-(3-chloro-4,5-dihydroisoxazol-5-yl)-alanine methyl ester;

N-Benzyloxycarbonyl-D,L-β-(3-chloro-4,5-dihydroisoxazol-5-yl)-alanine (3-(ethoxycarbonyl)phenyl) amide;

N-Benzyloxycarbonyl-D,L-β-(3-chloro-4,5-dihydroisoxazol-5-yl)-alanine (2-(ethoxycarbonyl)phenyl) amide;

N-Benzyloxycarbonyl-(L)-phenylalanyl-D,L-β-(3-chloro-4,5-dihydroisoxazol-5-yl)-alanine benzylamide;

D,L-β-(3-chloro-4,5-dihydroisoxazol-5-yl)-alanine (4-(ethoxycarbonyl)phenyl) amide, toluene sulfonic acid;

N-Benzyloxycarbonyl-D,L-β-(3-chloro-4,5-dihydroisoxazol-5-yl)-alanine (3-aminobenzyl) amide;

N-Benzyloxycarbonyl-D,L-β-(3-chloro-4,5-dihydroisoxazol-5-yl)-alanyl glycine ethyl ester;

N-tert-Butyloxycarbonyl-(L)-alanyl-D,L-β-(3-chloro-4,5-dihydroisoxazol-5-yl)alanine;

(L)-Alanyl-D,L-β-(3-chloro-4,5-dihydroisaxzol-5-yl)alanine;

N-Benzyloxycarbonyl-(L)-phenylalanyl-D,L-β-(3-chloro-4,5-dihydroisoxazol-5-yl)-alanyl-glycine;

N-((6-Methoxy-2-naphthyl)-2-propionyl)-D,L-β-(3-chloro-4,5-dihydroisoxazol-5-yl)-alanine 4-(ethoxycarbonyl)phenyl) amide; and N-Benzyloxycarbonyl-D,L-β-(3-chloro-4,5-dihydroisoxazol-5-yl)alanine (3,4-dimethoxybenzyl) amide.

It should be noted that individual stereoisomers, as well as mixtures thereof, are to be understood as within the scope of this invention. Thus, when a compound is named herein, the name should be understood to include the separate isomers of the named compound as well as mixtures of isomers thereof.

Utility and Administration

The compounds of Formula I are useful for treating mammals, particularly humans, which have a disease state characterized by elevated transglutaminase activity. Such disease states are exemplified by acne and cataracts, Alzheimer's and immunosuppressive diseases. The compounds of Formula I are particularly valuable because they are more potent and more selective than other known transglutaminase inhibitors. Further, the compounds of Formula I irreversibly inhibit transglutaminase.

The transglutaminase inhibitory activity of the compounds of this invention can be determined in vitro by accepted procedures described in the literature. See, e.g., DeYoung and Ballaron, *J. of Invest. Dermatology*, 79, (1982).

To determine the utility of the compounds of Formula I for treating acne in mammals, one can use the procedures described by DeYoung, et al. Another model that can be used is the Mexican hairless beagle dog. Many of these animals demonstrate a spontaneous acne-like condition with lesions similar to human open and closed comedones (Bedord, et al., *J. Invest. Dermatology*, 77, (1981)).

To determine the utility of the instant compounds in anthelminthic applications, see Examples 20 and 21.

The compounds of this invention are administered to a mammal or human in need thereof in a therapeutically effective dose. Such a dose is an amount sufficient to treat the disease state, i.e. inhibit transglutaminase.

The amount of active compound administered will of course, be dependent on the subject being treated, the nature and severity of the affliction, the molecular weight of the active ingredient, the manner of administration and the judgment of the prescribing physician. However, an effective dosage for a human is generally in the range of about 0.001 to about 100 mg/kg/day, preferably about 0.01 to about 10 mg/kg/day, and most preferably about 0.5 to about 5 mg/kg/day.

Administration of the active compounds and salts described herein can be via any of the accepted modes of administration for agents which have the intended therapeutic use. These methods include oral, parenteral, topical and otherwise systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For systemic administration via suppository, traditional binders and carriers include, e.g. polyalkalene glycols or triglycerides. Such suppositories may be formed from mixtures containing active ingredient in the range of 0.5%–10%; preferably 1–2%.

For the treatment of acne, the preferred manner of administration is topically using a convenient dosage form which can be readily applied to skin and will maintain the active compounds there until beneficial action can occur. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in this art; for example, see *Remington's Pharmaceutical Sciences*, Mack Publishing Company, Easton, Pa., 15th Edition, 1975.

The formulation will preferably contain from about 0.01 to about 10% (w/w) active component. Application will preferably be from 1 to 4 times daily for periods up to about 6 months. Dosage and frequency will of course depend on the severity of the patient's acne and the judgment of the patients physician; however, a preferable regimen would be twice daily application of a formulation containing 2.5% active component.

METHODS OF PREPARATION

The compounds of Formula I are prepared by performing a sequence of reactions as shown in the following reaction schemes. In the following reaction schemes, $R^I$ represents $R—(aa)_p—$ and $R^{II}$ represents $—(aa)_q—R^1$ as defined in the instant specification and appended claims, unless otherwise specified.

As shown in the following reaction schemes, the compounds of this invention are made by performing a (2+3) cycloaddition reaction between a preformed alkene substrate such as 2 or 3 and an halo-nitrile oxide which is prepared in situ from the corresponding dihaloformaldoxime according to the general methods of P. A. Wade, M. K. Pillay, and S. M. Singh, *Tetrahedron Lett.*, 4563 (1982); R. V. Stevens and R. P. Polniaszek, *Tetrahedron Lett.*, 39, 743 (1983); D. M. Vyas, Y. Chiang, and T. W. Doyle, *Tetrahedron Lett.*, 487 (1984); and A. A. Hagedorn, B. J. Miller, and J. O. Nagy, *Tetrahedron Lett.*, 229 (1980).

For example, dibromoformaldoxime is preferably added portion-wise to an aqueous solution of an olefinic alpha-amino acid containing an excess of NaHCO$_3$ according to the method of Hagedorn, et al. Purification by ion-exchange chromatography gives 3-bromo-4,5-dihydroisoxazol-5-yl-α-amino acids of structure 5 ($R_1$=H). (See Reaction Scheme II). Alternatively, an α-N-protected olefinic amino acid 2 (prepared by standard Schotten-Bauman conditions as found in Greenstein and Winitz) is reacted with dibromoformaldoxime plus NaHCO$_3$ as reported by Vyas or with dichloroformadoxime plus AgNO$_3$ as reported by Wade. Workup and purification by chromatography on silica gel gives product 5. (See Reaction Scheme II.)

For the chloro analogs, the general procedure involves the addition of small portions of AgNO$_3$ to a THF solution at 60°-65° C. containing dichloroformaldoxime and the alkene. Standard workup as described by Wade, et al. gives the desired 3-chloro-4,5-dihydroisoxazoles. The chloro analogs can also be prepared by performing an halogen exchange reaction with the 3-bromo-4,5-dihydroisoxazoles and a saturated HCl ether solution (see also K. C. Kelly, I. Schletter, S. J. Stein, W. Wierenga, *J. Am. Chem. Soc.*, 101, 1054, (1979)).

Further derivatives such as esters, amides, peptides, etc., of the resulting 3-halo-4,5-dihydroisoxazole product 5 or derivatives of 4 are made by standard peptide methodologies as found in *The Peptides; Analysis, Synthesis, and Biology*, Ed., E. Gross and J. Meienhofer, 1, (1979), and *Chemistry of the Amino Acids*, Ed., Greenstein and Winitz, John Wiley and Sons, 2, (1961).

The bromine atom in the 3-bromo-4,5-dihydroisoxazoles can be replaced by other groups such as alkoxy, alkylthio, alkylamino, or dialkylamino for instance, by reaction with sodium or lithium alkoxide, phenoxide, alkyl thiolate, phenyl thiolate, alkyl amides, or phenyl amides in THF or methanol at 20°-50° C. Other nitrile oxide reagents may be employed in the (2+3) cycloaddition reaction. For example, 3-phenylsulfonyl-4,5-dihydroisoxazoles are made by reacting benzenesulfonylcarbonitrile oxide with olefinic substrates (see P. A. Wade, H. K. Yeu, S. A. Hardinger, M. K. Pillay, N. V. Amin, P. D. Vail, and S. D. Morrow, *J. Org. Chem.*, 48, 1976 (1983), and P. A. Wade, and H. R. Hinney, *J. Amer. Chem. Soc.*, 101, 1320, (1979)). The sulfoxide and sulfone moieties are also made by oxidizing 3-alkylthio or 3-arylthio-4,5-dihydroisoxazoles with m-chloroperbenzoic acid (MCPBA) or with KMnO$_4$.

Turning now to Reaction Scheme I, the starting material, an unsaturated α-amino acid, is available commercially from Sigma Chemical Co., Chemical Dynamics Corp., Bachem, etc., or made by alkylating N,O-protected glycine at the α-position with an alkenyl halide (see G. Stork, A. Y. W. Leong, A. M. Touzin, *J. Org. Chem.*, 41, 3491 (1976), and S. Djuric, J. Venit, P. Magnus, *Tetrahedron Lett.*, 1787, (1981), and reference 6 therein). Alternatively, reaction of a vinyl or alkenyl Grignard with N-Cbz-α-chloro glycine methyl ester can be performed. (A. Castelhano, et al., *Tetrahedron Lett.*, 27, 2435, (1986)). In the case where n=0 in formula 1, the starting material may be obtained commercially from Sigma Chemical Co. or made according to the methods of A. Afzali-Ardakani and H. Rapoport, *J. Org. Chem.*, 45, 4817, (1980), or S. Hanessian and S. P. Sahoo, *Tetrahedron Lett.*, 1425, (1984).

Step A in Scheme I is directed to the substitution of the α-amino group using any reagent ($R^I Z$) suitable for introducing an N-protecting group ($R^I$). This step is a widely recognized standard operation in amino acid chemistry. For example, condensation of the α-amino acid 1 with BOC-ON or with benzyl chloroformate (both available from Aldrich Chemical Co.) provide 2 with $R^I$ being the tert-butoxycarbonyl or the benzyloxycarbonyl groups, respectively.

Steps B and E, in Schemes I and II respectively, involve derivatization of the carboxyl group in formulas 2 and 5 respectively, using a nucleophile ($R^{II}Y$) such as an alcohol or an amine. This step is a widely recognized standard operation in amino acid or peptide chemistry (see, *The Peptides*, as cited previously). First, the carboxyl groups in formulas 2 and 5 must be activated. The preferred method is the mixed anhydride coupling procedure utilizing isobutyl chloroformate/N-methyl piperidine as activating agents. Hence, the carboxyl group is activated with DCC, EDCI, N,N'-carbonyldiimidazole, or N-methyl morpholine, etc., and the resulting derivative treated with nucleophiles such as alcohols, amines, O-protected amino acids, peptides, etc., to give 3 and 4 in Schemes I and II, respectively. Steps B and E are carried out in an organic solvent such as ethyl acetate or methylene chloride at about −20° to 20° C.

Alternatively, derivatization of the carboxyl group, in 1 of Scheme I, may precede N-protection of the α-amino group and under these circumstances, reaction conditions may differ. Example 2 describes suitable conditions for introduction of an N-protecting group on an O-protected unsaturated α-amino acid.

Steps C and D, of Schemes I and II, respectively, involve performing a (2+3) cycloaddition reaction between the alkene group in 2 or 3 and a nitrile oxide reagent. For example, bromo nitrile oxide is generated in situ from dibromoformaldoxime and NaHCO$_3$. Dibromoformaldoxime is generated from glyoxic acid, hydroxyamine, and bromine in a one pot process according to the method of Vyas, et al. The cycloaddition is carried out in an organic solvent, preferably EtOAc, at 20°-30° C., preferably at 23° C. with 5-10 equivalents of NaHCO$_3$, but preferably 6 equivalents, and containing 2-5% water. The dibromoformaldoxime is added in small portions over a 10-60 minute interval, preferably 30 minutes. About 2-4 equivalents are usually required to convert all of the starting material to product 4 or 5. Isolation and purification of 5 is then accomplished by processing the reaction product in the usual manner for a carboxylic acid; in general, the organic phase is extracted with 5% NaHCO$_3$ and the combined aqueous portions are acidified to pH 3 with 5% HCl in a two phase system containing CH$_2$Cl$_2$. Further extractions of the aqueous phase with CH$_2$Cl$_2$ followed by washing the combined CH$_2$Cl$_2$ extracts with water, brine, drying over anhydrous MgSO$_4$, and concentration gives 5. Crystallization from chloroform/hexane gives pure 5 as a white crystalline substance.

Isolation of 4 involves a sodium bicarbonate washing of the organic reaction product in ethyl acetate, drying with anhydrous magnesium sulfate, concentration and purification on silica gel. Attempted crystallization from ethyl acetate/petroleum ether gives, in some cases, crystalline product. Otherwise, product 4 is isolated as an oil.

In the case where X is chlorine, the cycloaddition is preferably carried out in THF at 50°-70° C., preferably 60° C., by adding 4-6 equivalents of AgNO$_3$, preferably in small portion, to the alkene substrate and the dichloroformaldoxime reagent according to the method of Wade, et al. After total conversion of starting alkene, CH2Cl2 is added, the reaction mixture is filtered through celite and concentrated. Isolation and purification of product proceeds as above.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the Examples. However, other equivalent separation or isolation procedures could, of course, also be used.

The salt products are also isolated by conventional means. For example, the reaction mixtures may be evaporated to a dryness, and the salts can be further purified by conventional methods.

The compounds of Formula I in free base form may be converted to the acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula I may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent being used as the medium for the procedure.

The salt derivatives of the compounds of Formula I are prepared by treating the corresponding free acids of the compounds of Formula I with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of Formula I to base used are chosen to provide the ratio desired for any particular salt.

The compounds of the present invention may be prepared in either optically active form or as racemates or mixtures of diastereomers. Unless otherwise specified, the compounds described herein are all in the racemic form, or as a mixture of two diastereomers. The exception is the m-tyrosine analog since this amino acid is readily available commercially in D,L-form in which case a mixture of four isomers is obtained. However, the scope of the subject invention herein is not to be considered limited to mixtures of isomers, but to encompass the individual optical isomers of the compounds.

In most cases, individual isomers of Formula I are separated by semi-preparative HPLC on silica gel, eluting with ethyl acetate/hexane or other suitable solvents, or by performing fractional crystallizations.

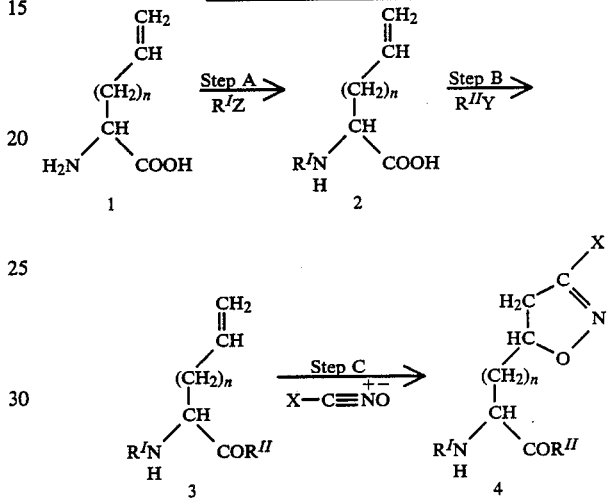

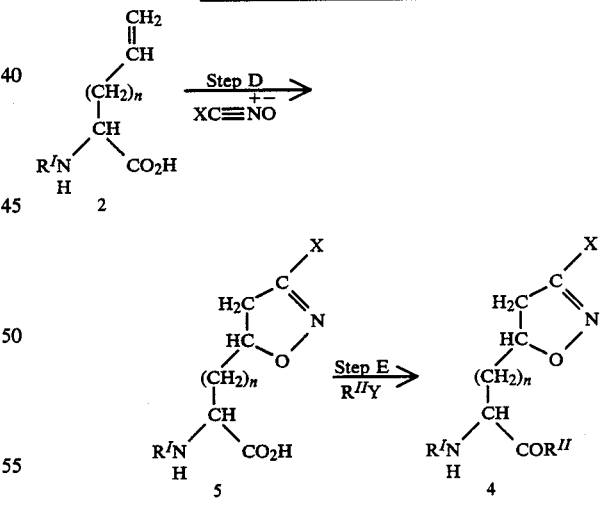

Scheme III is directed to the synthesis of derivatives of 4, such as would be obtained, for example, by the substitution of a different protecting group $R^r$, or the introduction of an N-protected amino acid, for $R^I$. A specific example would be replacement of $R^I$, e.g., where $R^I$ is Boc. Removal of the Boc group with trifluoroacetic acid or toluene sulfonic acid gives a compound of formula 6. Compound 6 is then coupled in the usual manner with an N-protected amino acid like N-CBZ-phenylalanine or is reacted with reagents that introduce a different N-protecting group from Boc.

REACTION SCHEME III

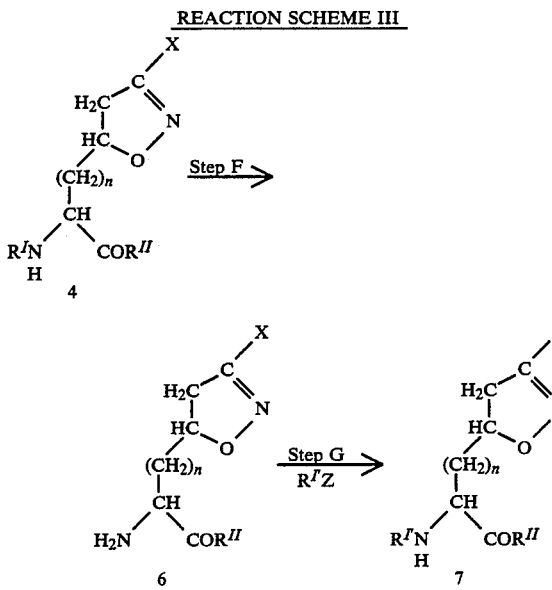

Scheme IV addresses those cases where $R^{II}$ is modified to become another group $R^{II'}$. For example, in the case where $R^I$ is CBZ and $R^{II}$ is $NHCH_2CO_2Et$ (Example 15 of experimental), hydrolysis with base gives $R^{II'}$ as $NHCH_2CO_2H$, a compound of formula 8.

REACTION SCHEME IV

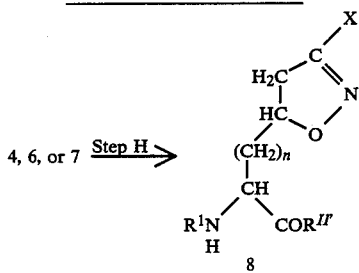

PREPARATIONS AND EXAMPLES

In the following examples, N-protected α-amino acids were supplied from commercial houses such as Sigma Chemical Co., Chemical Dynamics Corp., Bachem, Inc., etc., or were prepared by known procedures. For example, Cbz (M. Bergman, L. Zervas, *Ber. Dtsch. Chem. Ges.*, 65, 1192 (1932); see also Greenstein and Winitz); Box (M. Itoh, D. Hagiwara, 1192; see also Greenstein and Winitz); Boc (M. Itoh, D. Hagiwara, T. Kamiya, *Tetrahedron Lett.*, 4393, (1975)); FMOC (L. Lapatsanis, G. Milias, K. Froussios, M. Kolovos, *Synthesis*, 671, (1983)). The following experimental details are illustrative and should not be understood as limiting the scope of the invention.

PREPARATION 1 (Scheme 1, Step A)

N-tert-Butoxycarbonyl-D,L-allyl Glycine

To a stirred solution of D,L-allyl glycine, 7 gm, in 70 ml of 50% acetone/water and containing triethylamine, 12.8 ml, was added BOC-ON, 16.5 gm in portions. The mixture was left stirring for 2 hours and the acetone was then removed. The aqueous portion was further diluted and washed with 2×50 ml portions of EtOAc. The aqueous portion was then acidified in a two phase system containing 70 ml of $CH_2Cl_2$ with 10% HCl to pH 3. The organic portion was separated and the aqueous portion was further extracted with 2×50 ml of $CH_2Cl_2$. The combined organic extracts were pooled and washed once with 50 ml of water, brine, and dried over anhydrous $MgSO_4$. Filtration and concentration gave a pale yellow oil. IR (neat): 3420, 1708, 1160, 7356 cm-1. $^1H$ NMR (80 MHz, $CDCl_3$): delta 8.1–8.5 (broad s, 1H), 5.5–7.05 (m, 1H), 5.01–5.28 (m, 2H), 4.08–4.5 (m, 1H), 2.4–2.65 (dd, 2H), 1.42 (s, 9H).

Proceeding in a similar manner but using N-carbethoxyphthalimide, N-phthaloyl-D,L-allyl glycine was obtained.

PREPARATION 2 (Scheme I, Steps A & B combined)

N-Nicotinoyl-D,L-allyl Glycine Methyl Ester

To a stirred solution of nicotinic acid, 486 mg, in 10 ml of dry THF under nitrogen, was added N,N'-carbonyl-diimidazole, 640 mg. After evolution of $CO_2$ had ceased, the allyl glycine methyl ester hydrochloride, 653 mg, made from allyl glycine and HCl/MeoH (Fisher's method), was added. Four hours later, the reaction mixture was filtered to remove imidazole hydrochloride. The filtrate was concentrated and the product purified by chromatography on silica gel (50% EtOAc/hexane). IR (neat): 3300, 1740, 1655 cm-1. $^1H$ NMR (80 MHz, $CDCl_3$): delta 9.01 (d, 1H), 8.77 (dd, 1H), 8.12 (m, 1H), 7.3–7.52 (m, 1H), 6.7 (broad s, 1H), 5.5–6.02 (m, 1H), 4.76–5.34 (m, 3H), 3.81 (s, 3H), 2.59–2.81 (dd, 2H).

PREPARATION 3 (Scheme I, Step A)

N-Benzyloxycarbonyl-D,L-allyl Glycine

To a solution of D,L-allyl glycine, 19.6 gm, in 43 ml of 4N NaOH at 0° C. were added portion-wise 27 ml of carbobenzyloxy chloride and 51 ml of 4N NaOH over 30 min with vigorous stirring and maintaining a basic pH. The solution was then extracted once with 100 ml of ether, and the aqueous portion acidified to pH 3 with 10% HCl in a two phase system containing 100 ml of $CH_2Cl_2$. The aqueous portion was further extracted with $CH_2Cl_2$ (2×50 ml). The organic extracts were pooled, washed once with 20 ml of water, brine, dried over anhydrous $MgSO_4$, and concentrated to give product. $^1H$ NMR (80 MHz, $CDCl_3$): delta 2.55 (app. t, 2H, J=5.6 Hz, $CH_2$), 4.5 (m, 1H, CHN), 5.0–6.0 (m, 4H, NH, $CH_2=CH$), 5.1 (s, 2H, $PhCH_2$), 7.3 ppm (s, 5H, Ph). In the same manner but starting with either D- or L-allyl glycine, N-benzyloxycarbonyl-D-allyl glycine and N-benzyloxycarbonyl-L-allyl glycine were obtained, respectively.

PREPARATION 4-(Scheme I, Step B)

N-Benzyloxycarbonyl Allyl Alanine (4-(ethoxycarbonyl)phenyl) Amide

To 30 gm of N-benzyloxycarbonyl allyl glycine in 250 ml of ethyl acetate at 0° C., were added 20 gm of ethyl para-amino benzoate, 1.5 gm of DMAP, and 30 gm of EDCI. The reaction mixture was slowly brought to room temperature and left for two days. The reaction mixture was then washed once with 30 ml of each of water, 10% HCl, water, 5% $NaHCO_3$, brine, dried over anhydrous $MgSO_4$ and concentrated to give product as a crystalline mass.

PREPARATION 5 (Scheme I, Step B)

N-tert-Butoxycarbonyl-D-allyl Glycine (4-(ethoxycarbonyl)phenyl Amide

At −20° C. and under dry conditions and a nitrogen atmosphere, 2.7 ml of N-methyl piperidine were added dropwise to a CHCl$_3$ (200 ml) solution of N-tert-butoxycarbonyl-D-allyl glycine (prepared as in Example 1). After 5 minutes, 2.8 ml of isobutyl chloroformate were added dropwise, and after 15 minutes, 3.6 gm of ethyl para-amino benzoate were added dropwise. The reaction mixture slowly warmed up to room temperature and was left stirring for two days. Washing the reaction product once with 30 ml each of water, 5% HCl, water, 5% NaHCO$_3$, brine, drying with anhydrous MgSO$_4$, and concentration in vacuo gave product; $[\alpha]_D^{23} = +9.8°$ C. (c 0.04, CHCl$_3$).

EXAMPLE 1 (Scheme I, Step C)

N-tert-Butoxycarbonyl-D-beta-(3-bromo-4,5-dihydroxisoxazol-5-yl)alanine (4-(ethoxycarbonyl)phenyl) Amide Proceeding in the same manner as in Example 2, but employing N-tert-butoxycarbonyl-D-allyl glycine (4-(ethoxycarbonyl)phenyl) amide, the cycloaddition reaction gave the title compound which was purified by chromatography on silica gel, m.p. 116°–120° C.

Similarly, the cycloaddition reaction carried out with N-benzyloxycarbonyl-D,L-allyl glycine (4-(ethoxycarbonyl)phenyl) amide and dibromoformaldoxime gave N-benzyloxycarbonyl-beta-(3-bromo-4,5-dihydroisoxazol-5-yl) alanine (4-(ethoxycarbonyl)phenyl) amide, identical with the product formed in Example 4. When the cycloaddition was performed with dichloroformaldoxime and the resulting isomers were separated by HPLC on silica gel (40% EtOAc/hexane), N-benzyloxycarbonyl-beta-(3-chloro-4,5-dihydroisoxazol-5-yl) alanine (4-(ethoxycarbonyl)phenyl) amide was obtained; less polar isomer had m.p. 146°–148° C. and the more polar isomer had m.p. 139°–141° C.

In a similar manner, the following are made:

N-Tert-butoxycarbonyl-β-(3-phenylsulphonyl-4,5-dihydroisoxazol-5-yl)alanine (4-(ethoxycarbonyl)phenyl) amide;

N-benzyloxycarbonyl-β-(3-phenylsulphonyl-4,5-dihydroisoxazol-5-yl)alanine (4-(ethoxycarbonyl)phenyl) amide;

N-(4-methoxybenzylcarbonyl)-β-(3-chloro-4,5-dihydroisoxazol-5-yl)alanine (4-(ethoxycarbonyl)phenyl) amide;

N-(6-methoxy-2-naphthylpropionyl)-β-(3-chloro-4,5-dihydroisoxazol-5-yl)alanine (4-ethoxycarbonyl)phenyl) amide;

N-(6-methoxy-2-naphthylacetyl)-β-(3-chloro-4,5-dihydroisoxazol-5-yl)alanine (4-(ethoxycarbonyl)phenyl) amide; and N-benzyloxycarbonyl-phenylalanyl-β-(3-bromo-4,5-dihydroisoxazol-5-yl)alanine methyl ester.

EXAMPLE 2 (Scheme I, Step C or Scheme II, Step D)

N-Benzyloxycarbonyl-beta-(3-bromo-4,5-dihydroisoxazol-5-yl) Alanine

To a stirred solution of N-benzyloxycarbonyl-D,L-allyl glycine, 0.5 gm, in 30 ml of EtOAc and 1 ml of water, containing 1.7 gm of NaHCO$_3$, was added portion-wise at room temperature 2.0 gm of dibromoformaldoxime. After 2 hours, tlc indicated completeness of the reaction. The reaction mixture was then extracted with water and 5% NaHCO$_3$ (2×20 ml). The aqueous portions were pooled and acidified to pH 3.0 with 10% HCl in a two phase system containing 100 ml of CH$_2$Cl$_2$. The aqueous portion was further extracted with CH$_2$Cl$_2$ (2×20 ml) and the organic extracts pooled, washed once with 20 ml of water and brine. Drying over anhydrous MgSO$_4$, concentration, and crystallization from CHCl$_3$, product was obtained as a 1:1 mixture of diastereomers, m.p. 137°–138° C. IR (KBr): 3330, 3380, 3500–2500, 1740, 1710, 1670 cm-1. $^1$H NMR (80 MHz, CDCl$_3$): delta 2.0–2.4 (m, 2H, CH$_2$), 2.6–3.4 (m (ABX), 2H, CH$_2$), 4.5 (m, 1H, CHN), 4.7 (m, 1H, CHO), 5.1 (s, 2H, PhCH$_2$), 5.8 (broad s, 1H, NH), 7.3 ppm (s, 5H, Ph). Anal. Calcd. for C$_{14}$H$_{15}$BrN$_2$O$_5$: C, 45.3; H, 4.07; N, 7.55; Br, 21,.52. Found: C, 45.09; H, 4.08; N, 7.48; Br, 21.08. $^{13}$C NMR (20 MHz, CD$_3$COCD$_3$): delta 37.5 (CH$_2$), 47.9 (CH$_2$), 52.4 (CHN), 67.7 (PhCH$_2$O), 80.0, 80.7 (CHO), 128.7–129, 138.0 (Ph), 139.0, 139.2 (C=N), 158.4 (NHCO), 174.7, 175.0 ppm (CO$_2$H).

In a similar manner but starting with N-benzyloxycarbonyl D-allyl glycine, and separating the two resulting isomers by HPLC on silica gel (0.5% HOAc/4.5% iPrOH/CHCl$_3$), N-benzyloxycarbonyl-D-beta-(5-epsilon-3-bromo-4,5-dihydroisoxazol-5-yl) alanine were obtained. The more polar isomer (last to elute from the column) had $[\alpha]_D^{23} = +65.5°$ (c 0.026, EtOAc), whereas the least polar isomer had $[\alpha]_D^{23} = -34.5°$ (c 0.026, EtOAc). Similarly, L-allyl glycine gave N-benzyloxycarbonyl-L-beta-(5-epsilon-3-bromo-4,5-dihydroisoxazol-5-yl)-alanine. The more polar isomer had $[\alpha]_D^{23} = -62.6°$ (c 0.04, EtOAc), and the least polar isomer had $[\alpha]_D^{23} = +39.0°$ (c 0.018, EtOAc).

In a similar manner, the following compounds were also obtained:

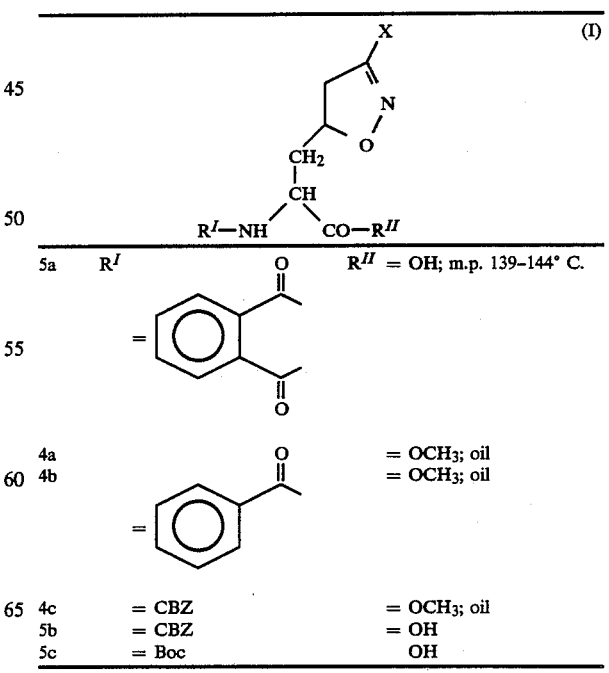

EXAMPLE 3 (Scheme II, Step D)

Beta-(3-bromo-4,5-dihydroisoxazol-5-yl) Alanine

To a solution of allyl glycine, 1.6 gm, and NaHCO$_3$, 7.0 gm, in 30 ml of water at 20° C., was added over one hour, dibromoformaldoxime, 8.5 gm, in small portions. After completion of the reaction (2–4 hours), the reaction mixture was washed with ether (2×20 ml), acidified to pH 3.0 with 10% HCl, and purified by ion-exchange chromatography (AG 50W×8, eluting with 20% pyridine-water). Crystallization from acetone-water gave product, m.p. 190°–195° (dec).

Alternatively, the title compound was obtained by treating N-tert-butoxycarbonyl-beta-(3-bromo-4,5-dihydroisoxazol-5-yl) alanine (prepared in Example 2, product 5c) with 20% CF$_3$COOH/CH$_2$Cl$_2$ at room temperature for 2 hours. Concentration, followed by ion-exchange chromatography as above, followed by purification by HPLC (reverse phase, eluting with water), and lyophilization, gave product as a fluffy white material. IR(KBr): 3400, 2400–3600, 1640, 1610, 1585 cm-1. $^1$H NMR (300 MHz, H$_2$O): delta 2.1–2.4 (m, 2H, CH$_2$CHN), 2.9–3.8 (ABX, 2H, CH$_2$CHO), 3.8–4.0 (m, 1H, CHN), 4.7–5.2 ppm (m, 1H, CHO).

EXAMPLE 4 (Scheme 2, Step E)

N-Benzyloxycarbonyl-beta-(3-bromo-4,5-dihydroisoxazol-5-yl)alanine
(4-(ethoxycarbonyl)phenyl) Amide To N-benzyloxycarbonyl-beta-(3-bromo-4,5-dihydroisoxazol-5-yl) alanine, 0.6 gm, in 50 ml of EtOAc at 0° were added 0.28 gm of ethyl para-aminobenzoate, 0.8 gm of EDCI and 40 mg of DMAP with stirring. The reaction mixture was then washed with 20 ml each of water, 5% HCl, water, 5% NaHCO$_3$, brine, dried over anhydrous MgSO$_4$, and concentrated to give product, m.p. 133°–142° C. IR (KBr): 3300, 1725, 1690, 1670. $^1$H NMR (80 MHz, CDCl$_3$): delta 1.35 (t, 3H, J=7.6 Hz, CH$_3$), 2.0–2.3 (m, 2H, CH$_2$CHN), 2.7–3.6 (m (ABX), 2H, CH$_2$CHO), 4.37 (q, 2H, J=7.5 Hz, CH$_2$O), 4.5–5.1 (m, 2H, CHN, CHO), 5.15 (s, 2H, PhCH$_2$O), 5.65–6.0 (broad d, NH) 7.35 (s, 5H, Ph of Cbz), 7.45–8.1 (symm. pattern, 4H, NHPhCO), 8.5 (broad s, 1H, NH).

In the same manner as above, the following compounds were made:

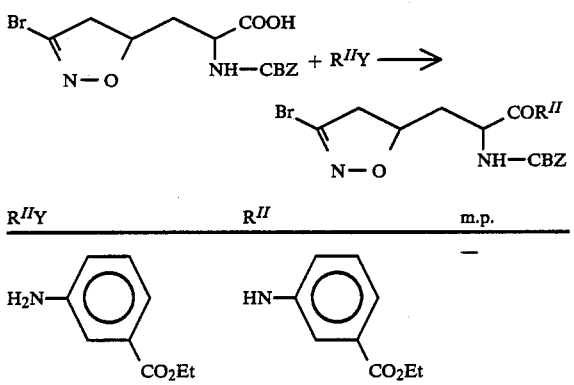

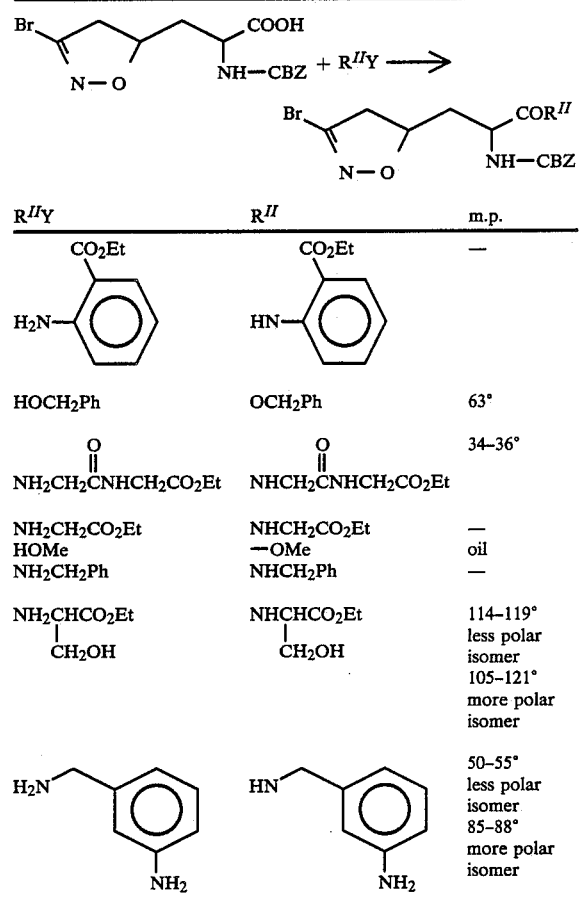

EXAMPLE 5 (Scheme 2, Step E)

N-Benzyloxycarbonyl-D,L-beta-(3-bromo-4,5-dihydroisoxazol-5-yl) Alanyl Glycine Ethyl Ester To a solution of N-benzyloxycarbonyl-D,L-beta-(3-bromo-4,5-dihydroisoxazol-5-yl) alanine, 1.2 gm, and glycine ethyl ester hydrochloride, 0.47 gm, in 50 ml of dry THF at 0° C., were added with stirring triethylamine, 0.56 ml, DMAP, 80 mg, and EDCI, 1.6 gm. Two hours later, the reaction mixture was brought to room temperature and left stirring overnight. The THF was then removed and the resulting oily residue was taken up in 60 ml of EtOAc and washed twice with 20 ml each of 5% HCl, water, 5% NaHCO$_3$, and brine. Drying over anhydrous MgSO$_4$ and concentration gave an oil which crystallized from EtOAC/pentane, m.p. 99°–101° C. IR (KBr): 3350, 1750, 1700, 1660 cm-1. $^1$H NMR (80 MHz, CDCl$_3$): delta 1.25 (t, 3H, J=7.0 Hz, CH$_3$), 2.05–2.25 (m, 2H, CH$_2$CHN), 2.7–3.6 (app. octet (two ABX systems, one for each diastereomer), 2H, CH$_2$CHO), 3.95–4.1 (m, 2H, CH$_2$CNH), 4.2 (q, 2H, J=7.0 Hz, CH$_2$O), 4.3–4.6 (m, 1H, CHN), 4.8–5.0 (m, 1H, CHO), 5.6 (broad d, 0.5H, J=7.3 Hz, NH of one diastereomer), 5.9 (broad d, 0.5H, J=7.6 Hz, NH of other diastereomer), 6.7–7.0 (broad s, 1H, NH), 7.35 ppm (s, 5H, Ph). $^{13}$C NMR (20 MHz, CDCl$_3$): delta 171.4, 171.2, 169.4 (CO$_2$, CCONH), 156.2, 156.0 (OC(O)NH), 137.8, 137.6 (BrC=N), 136.1, 136.0, 127.9–128.4 (Ph), 79.0, 79.1 (CHO), 67.2, 67.1 (CH$_2$O), 61.4 (PhCH$_2$), 52.5, 52.3 (CHN), 46.9, 46.8 (CH$_2$), 41.3

($CH_2NCO$), 37.6, 37.3 ($CH_2$), 14.1 ppm ($CH_3$). Anal. Calcd. for $C_{18}H_{22}BrN_3O_6$: C, 47.38; H, 4.86; N, 9.21; Br, 17.51. Found: C, 48.1; H, 5.21; N, 9.21; Br, 16.83.

EXAMPLE 6 (Scheme III, Step F)

L-Alanyl-beta-(3-bromo-4,5-dihydroisoxazol-5-yl) Alanine Trifluoroacetic Acid Salt N-tert-butoxycarbonyl-L-alanyl-beta-(3-bromo-4,5-dihydroisoxazol-5-yl) alanine, 0.8 gm, was taken in 50 ml of 20% $CF_3CO_2H/CH_2Cl_2$ at room temperature for 2 hours. Concentration gave a residue which was purified by HPLC, (reverse phase, eluting with water), to give two isomers as fluffy white material after lyophilization. $^1H$ NMR (80 MHz, $D_2O$): delta 1.55 (d, 3H, J=7.5 Hz, $CH_3$), 2.0–2.4 (m, 2H, $CH_2$), 2.9–3.7 (ABX, 2H, $CH_2CHO$), 4.1 (q, 2H, J=7.3 Hz, $OCH_2$), 4.4–5.0 ppm (m, CHN, CHO, plus HOD solvent peak). Most polar set of isomers from the HPLC: $^{13}C$ NMR (20 MHz, D20): delta 173.2, 173.1 (CO), 143.5 143.4 (BrC=N), 82.7, 81.8 (CHO), 51.8, 50.5 (broad, CHN), 49.0, 48.9 ($CH_2$), 38.6 ($CH_2$), 19.2 ppm ($CH_3$). Least polar isomer: $^{13}C$ NMR (20 MHz, D20): delta 180.2, 173.0 (CO), 143.5, 143.4 (BrCN), 83.6, 82.4 (CHO), 55.9, 54.9 (broad, CHN), 52.0 (CHN), 49.1, 48.7 ($CH_2$), 39.3, 38.9 ($CH_2$), 19.4 ($CH_3$).

Proceeding in the same manner (but employing HCl/ether in some cases at 0° C. or room temperature which results in hydrolysis of the Boc protecting group and exchange of the bromine atom for chlorine) the following compounds were obtained:

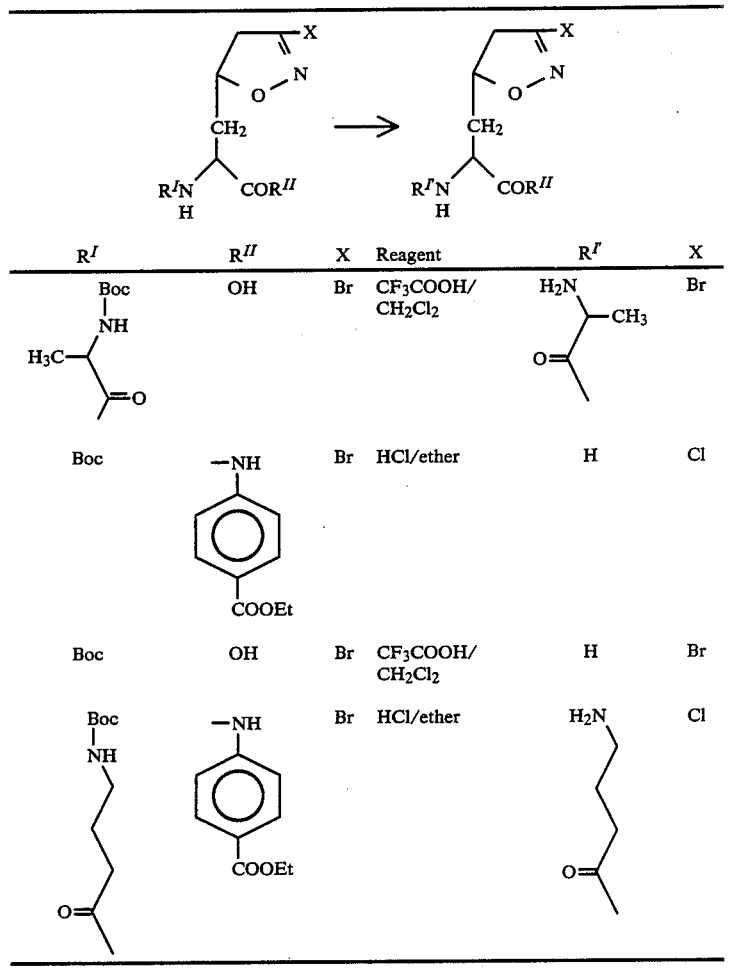

| $R^I$ | $R^{II}$ | X | Reagent | $R^{I'}$ | X |
|---|---|---|---|---|---|
| Boc-NH-CH(CH3)-C(=O)- | OH | Br | $CF_3COOH/CH_2Cl_2$ | $H_2N$-CH(CH3)-C(=O)- | Br |
| Boc | -NH-C6H4-COOEt | Br | HCl/ether | H | Cl |
| Boc | OH | Br | $CF_3COOH/CH_2Cl_2$ | H | Br |
| Boc-NH-(CH2)3-C(=O)- | -NH-C6H4-COOEt | Br | HCl/ether | $H_2N$-(CH2)3-C(=O)- | Cl |

EXAMPLE 7 (Scheme III, Step G)

N-tert-butoxycarbonyl-L-alanyl-beta-(3-bromo-4,5-dihydroisoxazol-5-yl) Alanine

To a water-THF (1:1) solution, 40 ml, of N-tert-butoxycarbonyl alanine N-hydroxysuccinimide ester, 0.6 gm, stirring at room temperature, was added 0.5 gm of beta-(3-bromo-4,5-dihydroisoxazol-5-yl) alanine and 0.7 ml of triethylamine. The reaction mixture was left overnight, the THF removed, the aqueous portion diluted to 40 ml and washed once with 20 ml of ethyl acetate. The aqueous portion was acifidied to pH 3.0 with 10% HCl in a two phase system containing 50 ml of $CH_2Cl_2$. The aqueous portion was further extracted with 2×20 ml of $CH_2Cl_2$ and the combined $CH_2Cl_2$ extracts were washed once with 20 ml of water, brine, dried over anhydrous $MgSO_4$ and concentrated to give a foam. $^1H$ NMR (80 MHz, $CDCl_3$): delta 1.4 (d, 3H, $CH_3$), 1.45 (s, 9H, t-butyl), 2.0–2.4 (m, 2H, $CH_2$), 2.7–3.6 (broad octet (ABX systems), 2H, $CH_2CHO$), 4.1–4.4 (m, 1H, CHN), 4.6–5.0 (m, 2H, CHN, CHO), 5.45 (broad s, 1H, NH), 7.4 (broad d, 1H, NH), 8.4 ppm (broad s, 1H, COOH).

EXAMPLE 8 (Scheme III, Step G)

N-[2(S)-6-methoxy-2-naphthylpropionyl]-L-β-(3-bromo-4,5-dihydroisoxazol-5-yl)alanine 4-(ethoxycarbonyl)phenyl amide To 500 mg of L-β-(3-bromo-4,5-dihydroisoxazol-5-yl)alanine 4-(ethoxycarbonyl)phenylamide toluene-sulphonic acid salt in 30 ml of EtoAc at 0°, was added 250 mg of 2(S)-6-methoxy-2-naphthylpropionic acid, 0.3 ml of NEt$_3$, 100 mg of DMAP, and 300 mg of EDCI with stirring. The reaction mixture was stirred at 0° for 2 hours and then overnight at room temperature. The reaction mixture was then washed with 20 ml portions of water, 5% HCl, water, 5% NaHCO$_3$, brine, dried over anhydrous MgSO$_4$, and concentrated to given an oil. Purification/separation was then accomplished by HPLC on silica gel, eluting with 40% EtOAc/hexane to give two isomers which solidified on concentration. $^1$H NMR (80 MHz, CDCl$_3$); less polar isomer: δ 1.32 (t, 3H, CH$_3$CH$_2$), 1.57 (d, 3H, CH$_3$CH), 2.22 (m, 2H, CH$_2$), 2.7–3.5 (m, 2H, CH$_2$CHO), 3.7–3.9 (m, 1H, CH), 3.85 (s, 3H, OMe), 4.3 (q, 2H, CH$_2$CH$_3$), 4.6–5.1 (m, 2H, CH, CHO), 6.9–7.8 (m, 11H, Ar, NHCH), 9.45 (s, 1H, NHPh). More polar isomer: δ 1.32 (t, 3H, CH$_3$CH$_2$), 1.59 (d, 3H, CH$_3$CH), 2.15 (m, 2H, CH$_2$), 2.7–3.5 (m, 2H, CH$_2$CHO), 3.7–3.9 (m, 1H, CH), 3.9 (s, 3H, OMe), 4.3 (q, 2H, CH$_2$CH$_3$) 4.6–5.1 (m, 2H, CH, CHO), 6.9–7.8 (m, 11H, Ar, NHCH), 9.2 (s, 1H, NHPh).

Proceeding in the same manner, following compounds were made:

N-benzyloxycarbonyl-L-β-(3-bromo-4,5-dihydroisoxazole-5-yl)alanine 4-(ethoxycarbonyl)phenyl amide;

N-benzyloxycarbonyl-L-phenylalanyl-D-β-(3-chloro-4,5-dihydroisoxazol-5-yl) alanine 4-(ethoxycarbonyl)phenyl amide, m.p. 181°–182° C.;

N-benzyloxycarbonyl-L-phenylalanyl-L-β-(3-bromo-4,5-dihydroisoxazol-5-yl)alanine 4-(ethoxycarbonyl)phenyl amide, m.p. 200°–203° C.;

N-benzyloxycarbonyl-glycyl-D-β-(3-chloro-4,5-dihydroisoxazol-5-yl) alanine 4-(ethoxycarbonyl)phenyl amide, m.p. 149°–152° C.; and N-tert-butoxycarbonyl-4-aminobutyryl-D-β-(3-chloro-4,5-dihydroisoxazol-5-yl)alanine 4-(ethoxycarbonyl)phenyl amide, m.p. 158°–162° C.

EXAMPLE 9 (Scheme IV, Step H)

N-Benzyloxycarbonyl-D,L-beta-(3-bromo-4,5-dihydroisoxazol-5-yl Alanyl Glycine

N-Benzyloxycarbonyl-D,L-beta-(3-bromo-4,5-dihydroisoxazol-5-yl) alanyl glycine ethyl ester, 0.2 gm, was taken in 20 ml of EtOH and 20 ml of 5% Na$_2$CO$_3$ at room temperature with vigorous stirring. After four days, the ethanol was removed, the residue diluted in 30 ml of water and washed with 10 ml of CH$_2$Cl$_2$. The aqueous portion was acidified to pH 3.0 with 10% HCl in a two phase system containing 50 ml of CH$_2$Cl$_2$. The aqueous portion was further extracted with 2×25 ml portions of CH$_2$Cl$_2$. The organic extracts were combined, washed once with 20 ml of water, brine, dried over anhydrous MgSO$_4$ and concentrated. Crystallization from CHCl$_3$/pentane gave product, m.p. 146°–147° C. IR (KBr): 3340, 3260, 2400–3600, 1725, 1705, 1635, 1560, 1525, 1250 cm-1. $^1$H NMR (80 MHz, acetone-d6): delta 2.0–2.3 (m, 2H, CH$_2$CHN), 2.5–3.3 (broad, COOH, NH), 2.8–3.6 (ABX, 2H, CH$_2$CHO), 3.97 (s, 2H, NCH$_2$CO), 4.15–4.6 (m, 1H, CHN), 4.7–5.1 (m, 1H, CHO), 5.2 (s, 2H, PhCH$_2$O), 6.6 (broad d, 1H, NH), 7.3 ppm (s, 5H, Ph).

EXAMPLE 10

Assay for Inhibition of Transglutaminases

Epidermal transglutaminase (TG) from bovine snout was isolated and partially purified by DEAE-Sepharose CL-6B ion exchange chromatography of the 10,000×g supernatant of a crude bovine snout epidermal homogenate. TG activity was eluted with a 0–0.7M NaCl gradient in 5 mM tris(hydroxymethyl)aminomethane (TRIS), 1 mM ethylenediaminetetraacetic acid (EDTA), pH 7.5 buffer. Fractions with TG activity were dialyzed against 5 mM TRIS, 1 mM EDTA at pH 7.5 and stored at −70° C. Inhibition was assayed by monitoring the rate of incorporation of a fluorogenic amine, specifically monodansylcadaverine, into CBZ-(L)-Glutaminyl-Glycine or dimethylcasein in the absence or presence of a compound of Formula 1, according to the procedures outlined below.

Liver transglutaminase from guinea pig liver was isolated and partially purified according to the procedure outlined in "Methods of Enzymology", Vol. 113, pp. 358–375, with minor modifications. The 105,000×g supernatant from the 15,000×g supernatant of a crude homogenate of guinea pig liver, was chromatographed on DEAE-Sepharose CL-6B. Enzymatic activity was eluted with a 0–1.0M NaCl gradient in 5 mM TRIS, 2 mM EDTA pH 7.5 buffer. Fractions containing activity were pooled, dialyzed against 50 mM TRIS-HCl, 2 mM EDTA, pH 7.5 buffer and concentrated, when necessary, by Amicon Ultrafiltration (PM 10 filters).

CONTINUOUS ASSAY: Fluorometric assay

A modification of the procedure by Lorand, et al. (Anal. Biochem., 44, 221–231 (1971)), wherein they report that the transglutaminase (Factor XIIIa) catalyzed covalent coupling of monodansylcadaverine into some proteins produces a shift in both the wavelength and intensity of fluorescence of the dansyl group.

Two mL of assay buffer (50 mM TRIS, 10 mM calcium chloride, pH 8.1, 5% v/v dimethylsulfoxide, 0.5 mM dithiothreitol, 25 micromolar monodansylcadaverine (Sigma Chemical Co.)) were thermostatted at 37° C. in a Perkin-Elmer 650-40 fluorimeter. Enzyme (5 to 20 microliters of a stock solution, sufficient to give approximately 0.1 fluorescence unit (FU) per minute uninhibited rate) and 5 microliters of a 1% w/v dimethylcasein (Serva Finebiochemica, Heidelberg) were introduced to initiate reaction and the increase in fluorescence was monitored continously. The fluorimeter excitation and emission wavelengths were 360 and 500 nm, respectively. After an initial (uninhibited) rate of TG catalyzed incorporation of monodansylcadaverine into dimethylcasein, the test compound was added (0.5 to 20 microliters of a stock solution in dimethylsulfoxide). Fluorescence monitoring was continued, typically for an additional 10–30 minutes.

DISCONTINUOUS ASSAY A

Assay using high pressure liquid chromatography with fluorometric detection

Potential transglutaminase inhibitors are routinely screened for their ability to inhibit the enzyme catalyzed incorporation of a fluorogenic amine, preferably monodansylcadaverine, into a glutamine containing peptide, preferably CBZ-(L)-Glutaminyl-Glycine (Sigma Chemical Co.).

One hundred and forty microliter aliquots of assay medium (50 mM TRIS, pH 8.1, 10 mM calcium chloride, 0.74 mM dithiothreitol, 1.48 mM monodansylcadaverine and sufficient enzyme to provide an uninhibited rate of 50–150 pmoles product/min) were thermostatted at 37° C. in capped microcentrifuge tubes. The test compound (10 microliter aliquots of a stock solution in dimethylsulfoxide) was added and at appropriate time intervals an excess of the glutaminyl substrate CBZ-(L)-Glutaminyl-Glycine (50 microliters of a 40 mM stock solution in 50 mM TRIS, 10 mM calcium chloride at pH 8.1) was introduced. This assay mixture was incubated for 30 minutes at 37° C. prior to addition of 80 microliters of quenching agent (100 mM EDTA and 40 micromolar Dansyl-Glycyl-(L)-Tryptophan (Sigma Chemical Co.)). Samples were diluted with 40 microliters of 1% HCl and 80 microliters of distilled water prior to HPLC analysis.

Product separation was accomplished by high pressure liquid chromatography of 20 microliter aliquots on a 25 cm Ultrasphere ODS 5 micron column (Regis, Ill.) with a Spectra Physics SP8700 system coupled to a SP8780 XR autosampler. Typically, gradient elution using acetonitrile:30 mM ammonium acetate (pH 4.5) mixtures of 36%:64% to 65%:35% at 1–1.3 mL per minute provided baseline separation of internal standard dansyl-Glycyl-(L)-Tryptophan and dansylated product, having retention times less than 10 minutes. A Kratos FS 950 Fluormat detector linked to a Spectra Physics 4100 Computing Integrator facilitated quantification of eluted products.

DISCONTINUOUS ASSAY B

The activity and inhibition of guinea pig liver transglutaminase was assayed by measurement of the rate of incorporation of hydroxylamine into simple glutaminyl peptide derivatives, preferably CBZ-(L)-Glutaminyl-Glycine (see Folk and Chung, "Methods in Enzymology", Vol. 113, pp. 359–361). The product is a peptide derivative of gamma-glutamyl hydroxyamine which, in the presence of acidic ferric chloride reagent, generates a colored complex having an extinction coefficient of 340M-1 cm-1 at 525 nm.

Prior to activity determination, guinea pig liver transglutaminase was activated anaerobically with 5 mM calcium chloride and 1 mM dithiothreitol at 25° C. In 1.5 mL Eppendorf microcentrifuge tubes, 140 microliters of activated transglutaminase and 7.4 microliters of the test compound in dimethylsulfoxide were incubated at 25° C. At appropriate time intervals, 20 microliter aliquots of incubation mixture were withdrawn and transferred to Eppendorf centrifuge tubes containing 200 microliters of assay medium (250 mM TRIS-Acetate, pH 6.0, 18.8 mM CBZ-(L)-Glutaminyl-Glucine, 6.25 mM calcium chloride, 1.25 mM EDTA, 125 mM hydroxylamine and 1.25 mM dithiothreitol) and 30 microliters of distilled water, thermostatted at 37° C. The concentration of product formed after 10–25 minutes incubation was determined by quenching with 250 microliters of acidic ferric chloride reagent and measurement of the absorbance at 525 nm using a Gilford 2600 UV/VIS spectrophotometer. Typical uninhibited samples provided sufficient product for 0.5 absorbance units at 525 nm.

CHARACTERIZATION OF INHIBITORS

The inactivation of transglutaminases by inhibitors of this invention is characterized by a time-dependent, irreversible decrease in the rate of product formation (continuous assay) or a decrease in the concentration of product ([P]) formed (discontinuous assays A and B). A second order rate constant (k/[I]) for the time dependent loss of enzymatic activity is our criteria for potency and is obtained as follows. For each compound, at a given concentration, first order rate constants (k) for time dependent loss of enzymatic activity were obtained by non-linear regression of [P] vs. time to either of the equations $[P] = Ae^{-(kt)} + B$ or $[P] = Ae^{(kt)}$.

Except in cases where solubility was limiting, k increased linearly with the concentration of inhibitor ([I]), and the desired second order rate constant, in units of $M^{-1}min^{-1}$, was obtained by linear regression analysis of k vs. [I].

In the following Examples 10 through 18, the active ingredient is the compound N-[(6-methoxy-2-naphthyl)-2'propionyl]-D,L-$\beta$-(3-bromo-4,5-dihydroisoxazol-5-yl)alanine (4-(ethoxycarbonyl)phenyl)amide. However, other compounds of the invention can be substituted therefor.

EXAMPLE 11

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1N) | q.s. to pH 7 |
| water (distilled, sterile) | q.s. to 20 ml |

EXAMPLE 12

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 13

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 14

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 15

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 16

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 17

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 18

| Ingredients | Topical Formulation grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. | 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 19

| Ingredients | Topical Formulation wt % |
| --- | --- |
| Active compound | 2.5 |
| Klucel (hydroxypropylcellulose) | 2.5 |
| diisopropyl adipate | 10 |
| ethanol | 80 |
| propylene glycol | 5 |

All of the ingredients except Klucel are first mixed together at room temperature, so that the active compound dissolves. Then the Klucel is dispersed and left to gel overnight.

EXAMPLE 20

In Vitro Assay Against Nippostronglus Braziliensis

N-Benzyloxycarbonyl-D,L-$\beta$-(3-bromo-4,5-dihydroisoxazol-5-yl)-alanine benzylamide was active against *Nippostronglus braziliensis* in an in vitro assay.

Rats were inoculated with 5,000 to 6,000 *N. braziliensis* third stage larvae subcutaneously. Seventy-two hours later rats were sacrificed and the fourth stage larvae harvested. Each drug was tested at 50 $\mu$g/ml against the fourth larval stage (L4) of *N. braziliensis* at approximately 50 L4/well. This mixture was incubated at 37° C. for a total of seven days and then read for activity. Parameters used to determine drug activity are motility, percent viability, and percent of L4 able to molt to the adult (percent cast formation). A compound is defined as active if (1) cast formation is reduced 50 percent or more or (2) viability and motility together are reduced 50 percent or more.

EXAMPLE 21

In Vivo Assay of Anthelmintic Activity Against Nematospiroides dubius and Hymenolepsis nana Male, Swiss-Webster mice were challenged with a mixed helminth infection of *Nematospiroides dubius* and *Hymenolepsis nana*. Starting 24 hours post-infection (p.i.) mice were treated for 11 days ad lib with N-Benzyloxycarbonyl-D,L-$\beta$-(3-bromo-4,5-dihydroisoxazol-5-yl)-alanine benzylamide mixed in the food at 1000 ppm. Animals were sacrificed on day 17 to examine parasite burden in the intestine. In each case, there was a significant percent reduction of parasites.

EXAMPLE 22

Cataract Therapy

Administration of N-benzyloxycarbonyl-D,L-$\beta$-(3-bromo-4,5-dihydroisoxazol-5-yl)-alanine (4-(ethoxycarbonyl)phenyl)amide, a potent inactivator of tissue transglutaminase, when administered by oral route in the diet at 0.05%, delayed the onset of galactose-induced cataracts.

EXAMPLE 23

Immunosuppressive Activity

Transglutaminase inactivator, N-benzyloxycarbonyl-D,L-$\beta$-(3-bromo-4,5-dihydroisoxazol-5-yl)-alanine (4-(ethoxycarbonyl)phenyl)amide, inhibited human T-lymphocyte transformation at $10^{-6}$ in vitro. The inhibition was not associated with cytotoxicity.

We claim:

1. A compound selected from the group consisting of:

N-Benzyloxycarbonyl-(L)-phenylalanyl-D,L-α-(3-bromo-4,5-dihydroisoxazol-5-yl)-glycine methyl ester;

N-Benzyloxycarbonyl-D,L-β-(3-bromo-4,5-dihydroisoxazol-5-yl)-alanyl serine ethyl ester;

N-Benzyloxycarbonyl-D,L-β-(3-bromo-4,5-dihydroisoxazol-5-yl)-alanine (4-(ethoxycarbonyl)phenyl)amide;

N-Benzyloxycarbonyl-(L)-phenylalanyl-D,L-β-(3-bromo-4,5-dihydroisoxazol-5-yl)-alanyl glycine ethyl ester;

N-Benzyloxycarbonyl-D,L-β-(3-bromo-4,5-dihydroisoxazol-5-yl)-alanine benzylamide;

N-Benzyloxycarbonyl-D,L-β-(3-bromo-4,5-dihydroisoxazol-5-yl)-alanine methyl ester;

N-Benzyloxycarbonyl-D,L-β-(3-bromo-4,5-dihydroisoxazol-5-yl)-alanine (3-(ethoxycarbonyl)phenyl) amide;

N-Benzyloxycarbonyl-D,L-β-(3-bromo-4,5-dihydroisoxazol-5-yl)-alanine (2-(ethoxycarbonyl)phenyl) amide;

N-Benzyloxycarbonyl-(L)-phenylalanyl-D,L-β-(3-bromo-4,5-dihydroisoxazol-5-yl)-alanine benzylamide;

N-Benzyloxycarbonyl-D-β-(3-bromo-4,5-dihydroisoxazol-5-yl)-alanine;

N-Benzyloxycarbonyl-L-β-(3-bromo-4,5-dihydroisoxazol-5-yl)-alanine;

N-Benzyloxycarbonyl-D,L-β-(3-bromo-4,5-dihydroisoxazol-5-yl)-alanine;

N-Nicotinyl-D,L-β-(3-bromo-4,5-dihydroisoxazol-5-yl)-alanine methyl ester;

N-Benzyloxycarbonyl-(L)-phenylalanyl-D,L-β-(3-bromo-4,5-dihydroisoxazol-5-yl)-alanine;

D,L-β-(3-bromo-4,5-dihydroisoxazol-5-yl)-alanine (4-(ethoxycarbonyl)phenyl) amide, toluene sulfonic acid;

N-Benzyloxycarbonyl-D,L-gamma-(3-bromo-4,5-dihydroisoxazol-5-yl)-homoalanine methyl ester;

N-Benzyloxycarbonyl-(L)-phenylalanyl-D,L-β-(3-bromo-4,5-dihydroisoxazol-5-yl)-alanine (4-(ethoxycarbonyl)phenyl)amide;

N-Benzyloxycarbonyl-D,L-β-(3-bromo-4,5-dihydroisoxazol-5-yl)-alanine (3-aminobenzyl) amide;

N-Benzyloxycarbonyl-D,L-β-(3-bromo-4,5-dihydroisoxazol-5-yl)-alanyl glycine ethyl ester;

N-Benzyloxycarbonyl-D,L-β-(3-bromo-4,5-dihydroisoxazol-5-yl)-alanine benzyl ester;

N-Benzyloxycarbonyl-D,L-β-(3-bromo-4,5-dihydroisoxazol-5-yl)-alanyl glycine;

N-Benzyloxycarbonyl-D,L-β-(3-bromo-4,5-dihydroisoxazol-5-yl)-alanyl glycyl glycyl ethyl ester;

N-Benzyloxycarbonyl-D,L-β-(3-chloro-4,5-dihydroisoxazol-5-yl)-alanine (4-(ethoxycarbonyl)phenyl) amide;

N-Tert-butyloxycarbonyl-D,L-β-(3-bromo-4,5-dihydroisoxazol-5-yl)-alanine (4-(ethoxycarbonyl)phenyl) amide;

D,L-β-(3-chloro-4,5-dihydroisoxazol-5-yl)-alanine (4-(ethoxycarbonyl)phenyl) amide;

N-Benzyloxycarbonyl-(L)-phenylalanyl-D,L-β-(3-chloro-4,5-dihydroisoxazol-5-yl)-alanine (4-(ethoxycarbonyl)phenyl) amide;

N-Benzyloxycarbonyl-glycyl-D,L-β-(3-chloro-4,5-dihydroisoxazol-5-yl)-alanine (4-ethoxycarbonyl)phenyl) amide;

N-Tert-butyloxycarbonyl-(L)-alanyl-D,L-β-(3-bromo-4,5-dihydroisoxazol-5-yl)alanine;

(L)-Alanyl-D,L-β-(3-bromo-4,5-dihydroisaxzol-5-yl)alanine;

N-benzyloxycarbonyl-(L)-phenylalanyl-D,L-β-(3-bromo-4,5-dihydroisoxazol-5-yl)-alanyl-glycine;

N-((6-methoxy-2-naphthyl)-2-propionyl)-D,L-β-(3-bromo-4,5-dihydroisoxazol-5-yl)-alanine 4-(ethoxycarbonyl)phenyl) amide; and N-benzyloxycarbonyl-D,L-β-(3-bromo-4,5-dihydroisoxazol-5-yl)alanine (3,4-dimethoxybenzyl) amide;

or an optical isomer, or a pharmaceutically acceptable salt of any of the foregoing.

2. The compound of claim 1 which is
N-Benzyloxycarbonyl-(L)-phenylalanyl-D,L-α-(3-bromo-4,5-dihydroisoxazol-5-yl)-glycine methyl ester;
or an optical isomer thereof, or a pharmaceutically acceptable salt thereof.

3. The compound of claim 1 which is
N-Benzyloxycarbonyl-D,L-β-(3-bromo-4,5-dihydroisoxazol-5-yl)-alanyl serine ethyl ester;
or an optical isomer thereof, or a pharmaceutically acceptable salt thereof.

4. The compound of claim 1 which is
N-Benzyloxycarbonyl-D,L-β-(3-bromo-4,5-dihydroisoxazol-5-yl)-alanine (4-(ethoxycarbonyl)phenyl)amide;
or an optical isomer thereof, or a pharmaceutically acceptable salt thereof.

5. The compound of claim 1 which is
N-Benzyloxycarbonyl-(L)-phenylalanyl-D,L-β-(3-bromo-4,5-dihydroisoxazol-5-yl)-alanyl glycine ethyl ester;
or an optical isomer thereof, or a pharmaceutically acceptable salt thereof.

6. The compound of claim 1 which is
N-Benzyloxycarbonyl-D,L-β-(3-bromo-4,5-dihydroisoxazol-5-yl)-alanine benzylamide;
or an optical isomer thereof, or a pharmaceutically acceptable salt thereof.

7. The compound of claim 1 which is
N-Benzyloxycarbonyl-D,L-β-(3-bromo-4,5-dihydroisoxazol-5-yl)-alanine methyl ester;
or an optical isomer thereof, or a pharmaceutically acceptable salt thereof.

8. The compound of claim 1 which is
N-Benzyloxycarbonyl-D,L-β-(3-bromo-4,5-dihydroisoxazol-5-yl)-alanine (3-(ethoxycarbonyl)phenyl) amide;
or an optical isomer thereof, or a pharmaceutically acceptable salt thereof.

9. The compound of claim 1 which is
N-Benzyloxycarbonyl-D,L-β-(3-bromo-4,5-dihydroisoxazol-5-yl)-alanine (2-(ethoxycarbonyl)phenyl) amide;
or an optical isomer thereof, or a pharmaceutically acceptable salt thereof.

10. The compound of claim 1 which is
N-Benzyloxycarbonyl-(L)-phenylalanyl-D,L-β-(3-bromo-4,5-dihydroisoxazol-5-yl)-alanine benzylamide;
or an optical isomer thereof, or a pharmaceutically acceptable salt thereof.

11. The compound of claim 1 which is the toluene sulfonic acid salt of
D,L-β-(3-bromo-4,5-dihydroisoxazol-5-yl)-alanine (4-(ethoxycarbonyl)phenyl) amide;

or an optical isomer or a pharmaceutically acceptable salt thereof.

12. The compound of claim 1 which is
N-Benzyloxycarbonyl-D,L-β-(3-bromo-4,5-dihydroisoxazol-5-yl)-alanine (3-aminobenzyl) amide;
or an optical isomer thereof, or a pharmaceutically acceptable salt thereof.

13. The compound of claim 1 which is
N-Benzyloxycarbonyl-D,L-β-(3-bromo-4,5-dihydroisoxazol-5-yl)-alanyl glycine ethyl ester;
or an optical isomer thereof, or a pharmaceutically acceptable salt thereof.

14. The compound of claim 1 which is
N-Tert-butyloxycarbonyl-(L)-alanyl-D,L-β-(3-bromo-4,5-dihydroisoxazol-5-yl)alanine;
or an optical isomer thereof, or a pharmaceutically acceptable salt thereof.

15. The compound of claim 1 which is
(L)-Alanyl-D,L-β-(3-bromo-4,5-dihydroisoxazol-5-yl)-alanine;
or an optical isomer thereof, or a pharmaceutically acceptable salt thereof.

16. The compound of claim 1 which is
N-benzyloxycarbonyl-(L)-phenylalanyl-D,L-β-(3-bromo-4,5-dihydroisoxazol-5-yl)-alanyl-glycine;
or an optical isomer thereof, or a pharmaceutically acceptable salt thereof.

17. The compound of claim 1 which is
N-((6-methoxy-2-naphthyl)-2-propionyl)-D,L-β-(3-bromo-4,5-dihydroisoxazol-5-yl)-alanine 4-(ethoxycarbonyl)phenyl amide;
or an optical isomer thereof, or a pharmaceutically acceptable salt thereof.

18. The compound of claim 1 which is
N-benzyloxycarbonyl-D,L-β-(3-bromo-4,5-dihydroisoxazol-5-yl)alanine (3,4-dimethoxybenzyl) amide
or an optical isomer thereof, or a pharmaceutically acceptable salt thereof.

19. A pharmaceutical composition comprising a therapeutically effective amount of a compound of claim 1 and a pharmaceutically acceptable excipient.

20. A pharmaceutical composition comprising a therapeutically effective amount of a compound of claim 4 and a pharmaceutically acceptable excipient.

21. A pharmaceutical composition comprising a therapeutically effective amount of a compound of claim 6 and a pharmaceutically acceptable excipient.

22. A pharmaceutical composition comprising a therapeutically effective amount of a compound of claim 17 and a pharmaceutically acceptable excipient.

* * * * *